(12) United States Patent
Turchi

(10) Patent No.: US 10,774,063 B2
(45) Date of Patent: Sep. 15, 2020

(54) MATERIALS AND METHOD FOR INHIBITING REPLICATION PROTEIN A AND USES THEREOF

(71) Applicant: INDIANA UNIVERSITY RESEARCH AND TECHNOLOGY CORPORATION, Indianapolis, IN (US)

(72) Inventor: John J. Turchi, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 195 days.

(21) Appl. No.: 15/524,830

(22) PCT Filed: Nov. 13, 2015

(86) PCT No.: PCT/US2015/060675
§ 371 (c)(1),
(2) Date: May 5, 2017

(87) PCT Pub. No.: WO2016/077752
PCT Pub. Date: May 19, 2016

(65) Prior Publication Data
US 2018/0305330 A1 Oct. 25, 2018

Related U.S. Application Data

(60) Provisional application No. 62/079,425, filed on Nov. 13, 2014.

(51) Int. Cl.
| | | |
|---|---|---|
| *C07D 401/04* | (2006.01) | |
| *A61P 35/00* | (2006.01) | |
| *C07D 403/04* | (2006.01) | |
| *C07D 231/06* | (2006.01) | |
| *A61K 45/06* | (2006.01) | |
| *A61K 47/26* | (2006.01) | |
| *A61K 47/38* | (2006.01) | |
| *C07D 401/14* | (2006.01) | |
| *C07D 413/14* | (2006.01) | |
| *A61K 9/00* | (2006.01) | |

(52) U.S. Cl.
CPC ............ *C07D 401/04* (2013.01); *A61K 45/06* (2013.01); *A61K 47/26* (2013.01); *A61K 47/38* (2013.01); *A61P 35/00* (2018.01); *C07D 231/06* (2013.01); *C07D 401/14* (2013.01); *C07D 403/04* (2013.01); *C07D 413/14* (2013.01); *A61K 9/0019* (2013.01); *A61K 9/0053* (2013.01)

(58) Field of Classification Search
None
See application file for complete search history.

(56) References Cited

U.S. PATENT DOCUMENTS

2013/0028989 A1   1/2013   Turchi et al.

FOREIGN PATENT DOCUMENTS

WO   2008045663 A2   4/2008

OTHER PUBLICATIONS

STN Registry Database entry for CAS RN 1311879-37-4; Entered STN Jul. 7, 2011; Accessed Dec. 10, 2018.*
PCT International Search Report and Written Opinion completed by the ISA/KR dated Jun. 29, 2016 and issued in connection with PCT/US2015/060675.
Mishra, Akaash K. et al., "Chemical inhibitor targeting the replication protein A-DNA interaction increases the efficacy of Pt-based chemotherapy in lung and ovarian cancer" Biochemical Pharmacology, 2015, vol. 93, No. 1, pp. 25-33, Nov. 4, 2014.
Wang, Xu et al. "A novel methodology for synthesis of dihydropyrazole derivatives as potential anticancer agents" Organic & Biomolecular Chemistry, 2014, vol. 12, No. 13, pp. 2028-2032, Jan. 22, 2014.
Raghav, Neera et al. "SAR studies of differently functionalized chalcones based hydrazones and their cyclized derivatives as inhibitors of mammalian cathepsin B and cathepsin H" Biooganic & Medicinal Chemistry, 2014, vol. 22, pp. 4233-4245, May 24, 2014.
Anciano Granadillo, Vitor J. et al "Targeting the OB-folds of replication protein A with small molecules" Journal of Nucleic Acids, 2010, vol. 2010 Article ID 304035, pp. 1-11.
Shuck, Sarah C. et al "Targeted inhibition of replication protein A reveals cytotoxic activity, synergy with chemotherapeutic DNA-damaging agents, and insight into cellular function" Cancer Res., 2010, vol. 70, No. 8, pp. 3189-3198.
Park, Hwangseo et al "A novel class of Hsp90 inhibitors isolated by structure-based virtual screening" Bioorganic & Medicinal Chemistry Letters, 2007, vol. 17, No. 22, pp. 6345-6349.

* cited by examiner

*Primary Examiner* — Alicia L Otton
(74) *Attorney, Agent, or Firm* — Barnes & Thornburg LLP

(57) ABSTRACT

Targeting uncontrolled cell proliferation and resistance to DNA damaging chemotherapeutics with at least one reagent has significant potential in cancer treatment. Replication Protein A, the eukaryotic single-strand (ss) DNA binding protein, is essential for genomic maintenance and stability via roles in both DNA replication and repair. Reported herein are small molecules that inhibit the in vitro, in vivo, and cellular ssDNA binding activity of RPA, thereby disrupting the eukaryotic cell cycle, inducing cytotoxicity and increasing the efficacy of chemotherapeutic agents damage DNA, and/or disrupt its replication and/or function. These results provide new insights into the mechanism of RPA-ssDNA interactions in chromosome maintenance and stability. This represents a molecularly targeted eukaryotic DNA binding inhibitor and demonstrates the utility of targeting a protein-DNA interaction as a means of studying the cell cycle and providing a therapeutic strategy for cancer treatment.

4 Claims, 20 Drawing Sheets

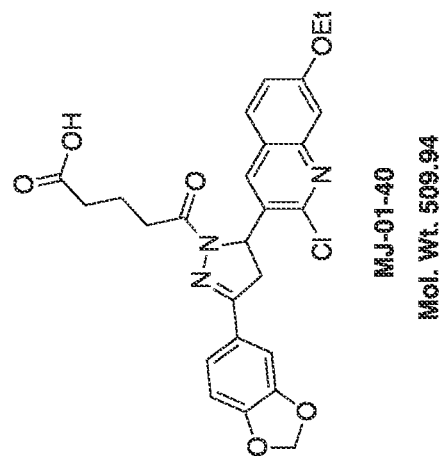
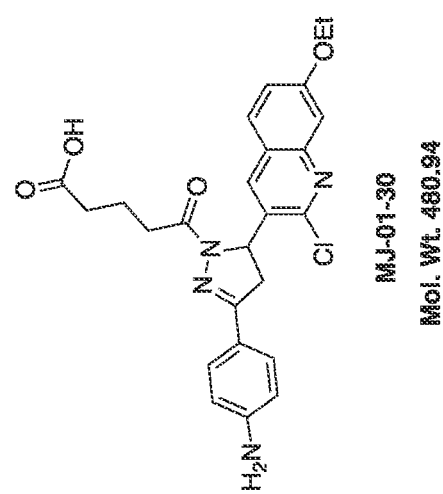
FIG. 16
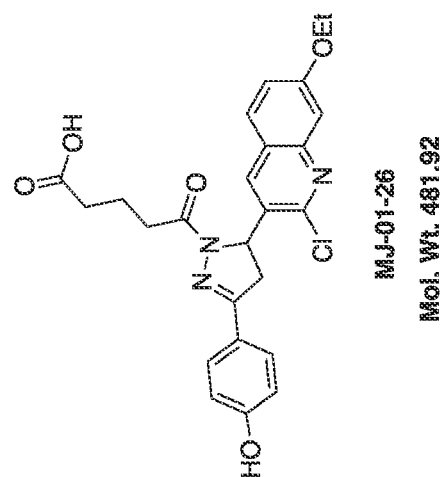

MATERIALS AND METHOD FOR INHIBITING REPLICATION PROTEIN A AND USES THEREOF

CROSS-REFERENCE TO RELATED APPLICATIONS

This application is a national stage entry under 35 USC § 371 of PCT International Application No. PCT/US2015/060675, filed Nov. 13, 2015, and claims the benefit under 35 USC § 119(e) to U.S. Provisional Patent Application No. 62/079,425, filed on Nov. 13, 2014, the disclosures of which are expressly incorporated by reference in their entirety.

STATEMENT OF GOVERNMENTAL RIGHTS

This invention was made with government support under CA180710 and CA162648 awarded by the National Institutes of Health. The Government has certain rights in the invention.

FIELD OF THE INVENTION

Some aspects of the invention relate to identifying molecules that at least partially inhibit the activity of the Replication Protein A, and these molecules can be used to treat hyper-proliferative diseases, including cancer.

BACKGROUND AND SUMMARY

Replication protein A (RPA) is the major human ssDNA binding protein and is required for both nucleotide excision repair (NER) and homologous recombination (HR). The RPA heterotrimer consists of 70 kDa, 32 kDa and 14 kDa subunits with the 70-kDa subunit containing the two major high affinity DNA binding domains (DBD) DBD A and B, as well as DBD C and F. DBD D and E are in the 32-kDa and 14-kDa subunit, respectively. Binding to short stretches of ssDNA (~8-10 nucleotides) is primarily mediated by DBD A and B, while intermediate length ssDNA (~12-23 nucleotides) also involves DBD C. Longer length ssDNA (~28-30 nucleotides) engages DBD D in addition to DBDs A, B and C. RPA plays essential and non-redundant roles in both NER and HR, apart from its role in replication and DNA damage checkpoint activation. Each of these roles requires binding of RPA to ssDNA, making RPA-DNA interaction a promising target for anti-cancer therapeutic activity in combination with Pt-containing cancer drugs, for example, cisplatin.

The ssDNA binding activity of RPA is required for several DNA metabolic pathways including DNA replication, recombination and repair. High affinity interactions with DNA are sustained by the numerous oligosaccharide/oligonucleotide binding (OB)-folds present on each of the three subunits. The DNA binding pocket of a single OB-fold accommodates 3-4 bases of ssDNA. The main OB-folds, DNA binding domains A and B (DBD-A and DBD-B) are present in the central region of the p70 subunit and contribute most of the binding energy for RPA-ssDNA interactions. Individual OB-folds are compact modular domains populated with hydrophobic and basic amino acids. These structural features make the OB-folds an attractive target for development of small molecule inhibitors (SMIs) of DNA binding activity. Given RPA's central role in cell growth and DNA repair, it is an attractive target for the development of compounds that can interfere with its activity. Some aspects of the instant invention include compounds that interact with RPA and methods of using the same to influence cell growth and death.

Platinum-based chemotherapeutics exert their therapeutic efficacy via the formation of DNA adducts which interfere with DNA replication, transcription and cell division and ultimately induce cell death. Repair and tolerance of these Pt-DNA lesions by NER and HR can substantially reduce the effectiveness of therapy. Inhibition of these repair pathways, therefore, holds the potential to sensitize cancer cells to Pt treatment and increase clinical efficacy. Replication Protein A (RPA) plays essential roles in both NER and HR, along with its role in DNA replication and DNA damage checkpoint activation. Each of these functions is, in part, mediated by RPA binding to single-stranded DNA (ssDNA).

In some embodiments of the present disclosure, the synthesis and characterization of derivatives of RPA small molecule inhibitors and their activity in models of epithelial ovarian cancer (EOC) and non-small cell lung cancer (NSCLC) are shown. In some embodiments, synthesized analogs of RPA inhibitor TDRL-505 are disclosed along with the structure activity relationships. Certain compounds, such as, for example, TDRL-551, exhibit a greater than 2-fold increase in in vitro activity. TDRL-551 showed synergy with Pt in tissue culture models of EOC and in vivo efficacy, as a single agent and in combination with platinum, in a NSCLC xenograft model. Data demonstrate the utility of RPA inhibition in EOC and NSCLC and the potential in developing anticancer therapeutics that target RPA-DNA interactions.

Platinum (Pt)-based combination chemotherapy has been the front-line treatment for a variety of malignancies including testicular, lung, and ovarian cancer. However, resistance to Pt-based regimens remains a major limitation in the successful treatment for many of these cancers including epithelial ovarian cancer (EOC) and non-small cell lung cancer (NSCLC). More than 80% of EOC patients relapse with Pt-resistant disease, where second line therapies are largely ineffective. Thus, ovarian cancer has been clinically designated as the most deadly gynecological cancer owing to extremely poor prognosis and overall low survival rates. The clinical efficacy of cisplatin is a function of its ability to cross-link DNA thereby blocking DNA replication, transcription and cell division. Ultimately Pt-treatment induces apoptosis, however, the balance between DNA damage and DNA repair dictates the extent of tumor death. While Pt-resistance is multifactorial, increased DNA repair is a major contributor. Hence, exploiting DNA repair as a target to sensitize cells to Pt-based chemotherapy holds immense potential for increasing the survival rates in cancer therapy.

Repair and tolerance of cisplatin-DNA adducts occur primarily via nucleotide excision repair (NER) and homologous recombination (HR). Approximately 95% of Pt-DNA lesions formed by cisplatin are intrastrand crosslinks with the remaining ~5% being interstrand crosslinks and a small number of mono-lesions. There is evidence for and against each lesion type being the cytotoxic lesion caused by cisplatin. Interstrand lesions are less abundant and repaired more efficiently than intrastrand lesions, and involve the HR pathway in conjunction with the FANC protein complex (a group of proteins associated with Fanconi anemia). Interstand adducts are more cytotoxic with estimates to as few as 20 interstrand crosslinks causing cell death if left unrepaired. While more abundant and repaired slower, intrastrand lesions are better tolerated via HR and bypass polymerases. Repair of intrastrand crosslinks occurs via the NER pathway. Therefore, while the exact lesion responsible for clinical efficacy remains to be determined, what is clear is that both NER and HR have differential and contributory roles in the cellular sensitivity to cisplatin.

Structural analysis of RPA reveals unique protein-DNA interactions that would facilitate the design of potent and selective small molecule inhibitors (SMIs). It has been also shown that genetic mutants of RPA display defects in DNA repair without impacting DNA replication and vice versa. This separation of function can be exploited by using chemical probes that exclusively interfere with the DNA repair pathway and that, in conjunction with DNA-damaging agents, would offer a new possibility for cancer treatment. Both reversible and irreversible chemical inhibitors of RPA have been reported. The reversible inhibitor TDRL-505 exhibits synergistic effects with DNA damaging agents in a lung cancer cell model. This small molecule hinders the binding of DBD A and B of RPA to ssDNA, which according to in silico docking analysis occurs as a consequence of its interaction with DBD B and the DBD A-B interdomain. In the present disclosure, a series of analogs of TDRL-505 have been screened in vitro and their activity in an EOC cell culture model has been evaluated. Structure activity relationship (SAR) data led to at least one enhanced compound, TDRL-551. Herein disclosed is in vitro, cellular and in vivo activity of RPA inhibitor TDRL-551 in models of lung and ovarian cancer.

A first set of embodiments of the present disclosure, includes at least one compound of Formula I or a pharmaceutically acceptable salt thereof, or a metabolite thereof:

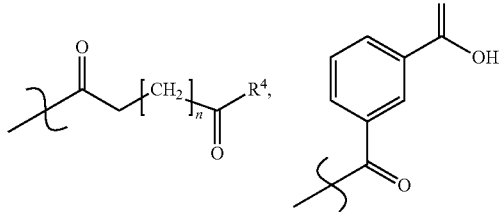

I

In a first embodiment of the first set of embodiments: $R^1$ is

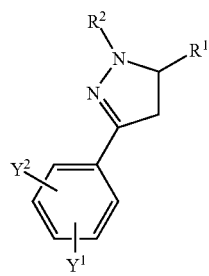

or phenyl optionally substituted with 1 to 3 $R^5$;
$R^2$ is

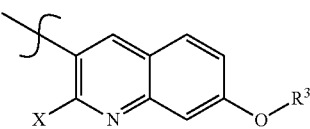

or phenyl optionally substituted with —C(=O)OH or —SO$_2$NH$_2$;

n is 1, 2, or 3;

$R^3$ is $C_1$-$C_6$ alkyl, or alternatively $R^3$ forms a dioxolane ring sharing two carbon atoms with the quinolone ring of $R^1$;

$R^4$ is hydroxyl, $C_1$-$C_6$ alkoxy, —O—CH$_2$-phenyl, morpholinyl, 1-methylpiperazinyl, 1-amino-cyclopropyl, amino-methyl-cyclopropyl;

$R^5$ is $C_1$-$C_6$ alkyl or $C_1$-$C_6$ alkoxy;

X is halogen; and $Y^1$ and $Y^2$ are independently selected from H, halogen, hydroxyl, $C_1$-$C_6$ alkyl, $C_1$-$C_6$ alkoxy, $C_1$-$C_6$ haloalkoxy, —NH$_2$, —NO$_2$, —OC(=O)C(H)=CH$_2$, carboxyl, or tetrazolyl; alternatively, $Y^1$ and $Y^2$ are taken together to form a dioxolane ring sharing two carbons with the phenyl ring of Formula I;

A second embodiment includes the compound of the first embodiment, wherein $R^1$ is

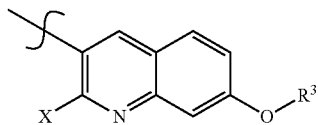

and X is chlorine. In an even more particular embodiment, $R^3$ is $C_1$-$C_6$ alkyl, and even more particularly, $R^3$ is ethyl.

A third embodiment includes the compound of the first embodiment, wherein $R^1$ is phenyl optionally substituted with 1 to 3 $R^5$. In an even more particular embodiment, $R^1$ is unsubstituted phenyl. In another more particular embodiment, $R^1$ is phenyl substituted with 1-2 $C_1$-$C_6$ alkoxy, and more particularly, 1-2 methoxy.

A fourth embodiment includes the compound of any of the first to the third embodiments, wherein $R^2$ is

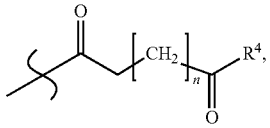

In an even more particular embodiment, n is 2. In another more particular embodiment, n is 2. In another more particular embodiment, $R^4$ is hydroxyl. In another more particular embodiment, $R^4$ is $C_1$-$C_6$ alkoxy, and even more particularly ethoxy. In another more particular embodiment, $R^4$ is —O—CH$_2$-phenyl. In another more particular embodiment, $R^4$ is morpholinyl. In another more particular embodiment, $R^4$ is 1-methylpiperazinyl. In another more particular embodiment, $R^4$ is 1-amino-cyclopropyl. In another more particular embodiment, $R^4$ is amino-methyl-cyclopropyl A fifth embodiment includes the compound of any of the first to the third embodiments, wherein $R^2$ is

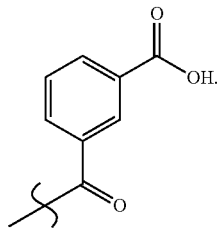

A sixth embodiment includes the compound of any of the first to the third embodiments, wherein $R^2$ is or phenyl optionally substituted with —C(=O)OH or —SO$_2$NH$_2$. In a more particular embodiment, $R^2$ is phenyl substituted with —C(=O)OH or —SO$_2$NH$_2$. In another more particular embodiment, $R^2$ is phenyl substituted with —C(=O)OH. In yet another more particular embodiment, $R^2$ is phenyl substituted with —SO$_2$NH$_2$.

A seventh embodiment includes the compound of any of the first to sixth embodiments, wherein $Y^1$ and $Y^2$ are independently selected from H, halogen, hydroxyl, $C_1$-$C_6$ alkyl, $C_1$-$C_6$ alkoxy, $C_1$-$C_6$ haloalkoxy, —NH$_2$, —NO$_2$, —OC(=O)C(H)=CH$_2$, carboxyl, or tetrazolyl. In a more particular embodiment, $Y^1$ is H and $Y^2$ is a halogen, and even more particularly, $Y^1$ is H and $Y^2$ is iodine, or $Y^1$ is H and $Y^2$ is chlorine, or $Y^1$ is H and $Y^2$ is bromine. In another more particular embodiment, $Y^1$ is H and $Y^2$ is $C_1$-$C_6$ alkyl, and even more particularly, $Y^1$ is H and $Y^2$ is methyl. In another more particular embodiment, $Y^1$ is H and $Y^2$ is $C_1$-$C_6$ alkoxy, and even more particularly, $Y^1$ is H and $Y^2$ is methoxy. In another more particular embodiment, $Y^1$ and $Y^2$ are each independently $C_1$-$C_6$ alkoxy, and even more particularly, $Y^1$ and $Y^2$ are each methoxy. In another more particular embodiment, $Y^1$ is H and $Y^2$ is —OC(=O)C(H)=CH$_2$. In another more particular embodiment, $Y^1$ is H and $Y^2$ is tetrazolyl. In another more particular embodiment, $Y^1$ is H and $Y^2$ is —NO$_2$. In another more particular embodiment, $Y^1$ is H and $Y^2$ is NH$_2$. In another more particular embodiment, $Y^1$ is H and $Y^2$ is —OH.

An eighth embodiment includes the compound of any of the first to sixth embodiments, wherein $Y^1$ and $Y^2$ are taken together to form a dioxolane ring sharing two carbons with the phenyl ring of Formula I.

A second set of embodiments of the present disclosure, includes at least one compound according to Formula II or a pharmaceutically acceptable salt thereof, or a metabolite thereof:

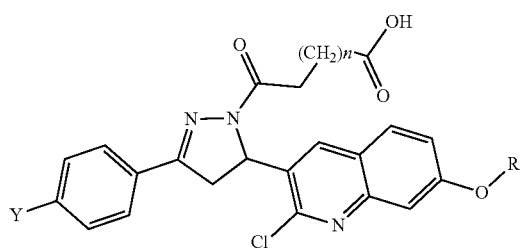

II

In a first embodiment of the second set of embodiments, R is $C_1$-$C_6$ alkyl; Y is a substituent selected from the group consisting of: fluorine, iodine, chlorine, and —OCF$_3$; and n is 1, 2, or 3;

A second embodiment of the second set of embodiments includes the compound of the first embodiment, wherein R is methyl or ethyl.

A third embodiment of the second set of embodiments includes the compound of the first or second embodiment, wherein Y is selected from fluorine, iodine, and chlorine. In a more particular embodiment, Y is fluorine. In another more particular embodiment, Y is iodine. In another more particular embodiment, Y is chlorine.

A fourth embodiment of the second set of embodiments includes the compound of the first or second embodiment, wherein Y is —OCF$_3$.

A fifth embodiment of the second set of embodiments includes the compound of any of the first through fourth embodiments, wherein n is 2.

A third set embodiments of the present disclosure, includes the compound according to any of the first and/or second sets of embodiments, wherein the compound is a compound selected from the group consisting of: TDRL-540, TDRL-539, TDRL-551, TDRL-557, and TDRL-652, NG-01-04, NG-01-02, NG-01-24, NG-01-25, or a pharmaceutically acceptable salt thereof, or a metabolite thereof.

A fourth set embodiments of the present disclosure, includes the compound according to any of the first, second, and/or third sets of embodiments, wherein said compound is compound TDRL-551, or a pharmaceutically acceptable salt thereof or a metabolite thereof.

A fifth set of embodiments of the present disclosure includes the compound according to any of the first, second, third, and/or fourth sets of embodiments, wherein the compound at least partially inhibits Replication Protein A.

A sixth set of embodiments of the present disclosure includes at least one method of reducing the activity of a protein, comprising the steps of: providing a compound of any one of the first, second, third, and/or fourth sets of embodiments, or a pharmaceutically acceptable salt or metabolite thereof, wherein the compound binds to Replication Protein A or is metabolized into a chemical that binds to Replication Protein A; and contacting said compound with at least one isoform of Replication Protein A.

A seventh set of embodiments of the present disclosure includes at least one of the methods according to any of the sixth set of embodiments, wherein the contacting step between either the compound of any one of the first, second, third, and fourth embodiment, or a pharmaceutically acceptable salt or metabolite thereof, and the at least one isoform of Replication Protein A occurs in vivo or in vitro.

An eighth set of embodiments of the present disclosure includes at least one method of altering eukaryotic cell cycle-progression, comprising the steps of: providing a compound of any one of the first, second, third, and/or fourth sets of embodiments, or a pharmaceutically acceptable salt or metabolite thereof, wherein the compound interferes with eukaryotic cell cycle-progression or is metabolized into a chemical that interferes with eukaryotic cell cycle-progression; and contacting the compound with at least one eukaryotic cell.

A ninth set of embodiments of the present disclosure includes at least one method according to any of the eighth set of embodiments, wherein the contacting step between said compound of any one of the first, second, third, and/or fourth sets of embodiments, or a pharmaceutically acceptable salt or metabolite thereof, and the eukaryotic cell occurs in vivo or in vitro.

A tenth set of embodiments of the present disclosure includes at least one method of treating cancer, comprising the steps of: providing a compound of any of the first, second, third, and/or fourth sets of embodiments, or a pharmaceutically acceptable salt or metabolite thereof, wherein the compound interferes with the cell cycle of a cancer cell or is metabolized into a chemical that interferes with the cell cycle of a cancer cell; and contacting the compound with at least one cancer cell.

An eleventh set of embodiments of the present disclosure includes at least one method according to any of the tenth set of embodiments, wherein the contacting step between said compound of any of the first, second, third, and/or fourth sets of embodiments, or a pharmaceutically acceptable salt or metabolite thereof, and the cancer cell occurs in vivo in in vitro.

A twelfth set of embodiments of the present disclosure includes at least one set of methods according to any of the tenth and/or eleventh sets of embodiments, wherein the cancer cell is an epithelial ovarian cancer cell or a non-small cell lung cancer cell.

A thirteenth set of embodiments of the present disclosure includes at least one method of treating a disease, comprising the steps of: providing at least one compound of any of the first, second, third, and/or fourth sets of embodiments, or a pharmaceutically acceptable salt or metabolite thereof, wherein the compound is effective for the treatment of at least one disease; and administering at least one therapeutically effective dose of the compound to a patent diagnosed with a specific disease.

A fourteenth set of embodiments of the present disclosure includes at least one of the methods according to any of the thirteenth set of embodiments, wherein the compound is suitable for administration to a patient.

A fifteenth set of embodiments of the present disclosure includes at least one method according to any of the thirteenth set of embodiments, wherein the compound is suitable for administration to a patient orally.

A sixteenth set of embodiments of the present disclosure includes at least one method according to any of the thirteenth set of embodiments, wherein the compound is suitable for administration to a patient intraperitoneally.

A seventeenth set of embodiments of the present disclosure includes at least one method according to any one of the thirteenth, fourteenth, and/or sixteenth sets of embodiments, wherein the compound is in a formulation, and wherein said formulation includes methylcellulose.

An eighteenth set of embodiments of the present disclosure includes at least one method according to any one of the thirteenth, fourteenth, and/or sixteenth sets of embodiments, wherein the compound is in a formulation, and wherein said formulation includes Tween-80.

A nineteenth set of embodiments of the present disclosure includes at least one method of treating a patient, comprising the steps of: providing at least one compound of any of the first, second, third, and/or fourth sets of embodiments, or a pharmaceutically acceptable salt or metabolite thereof, wherein said compound is formulated for treatment of a human or an animal patient; and administering at least one therapeutic dose of the compound to the human or animal patient.

A twentieth set of embodiments of the present disclosure includes at least one of the methods according to any of the nineteenth set of embodiments, wherein the patient is also treated with a therapeutically effective dose of at least one compound of any of the first, second, third, and fourth embodiment, or a pharmaceutically acceptable salt or metabolite thereof, wherein said compound damages DNA directly or that inhibits topoisomerase II.

A twenty-first set of embodiments of the present disclosure includes at least one method according to any of the nineteenth and/or twentieth sets of embodiments, wherein the patient is also treated with a therapeutically effective dose of at least one compound selected from the group consisting of: Cisplatin, Etoposide, Busulfan, Bendamustine, Carboplatin, Carmustine, Chlorambucil, Cyclophosphamide, Dacarbazine, Daunorubicin, Decitabine, Doxorubicin, Epirubicin, Etoposide, Idarubicin, Ifosfamide, Irinotecan, Lomustine, Mechlorethamine, Melphalan, Mitomycin C, Mitoxantrone, Oxaliplatin, Temozolomide, and Topotecan.

A twenty-second e set of embodiments of the present disclosure includes at least one method according to any one of the nineteenth, twentieth, and/or twenty first set of embodiments, wherein said therapeutically effective dose is in the ranges selected from the group consisting of: about 10 mg of said compound per $kg^{-1}$ to about 1000 mg of said compound per $kg^{-1}$ of the patient's body weight, about 10 mg of said compound per $kg^{-1}$ to about 500 mg of said compound per $kg^{-1}$ of the patient's body weight, about 20 mg of said compound per $kg^{-1}$ to about 450 mg of said compound per $kg^{-1}$ of the patient's body weight, about 30 mg of said compound per $kg^{-1}$ to about 400 mg of said compound per $kg^{-1}$ of the patient's body weight, about 40 mg of said compound per $kg^{-1}$ to about 350 mg of said compound per $kg^{-1}$ of the patient's body weight, and about 50 mg of said compound per $kg^{-1}$ to about 300 mg of said compound per $kg^{-1}$ of the patient's body weight.

A twenty-third set of embodiments of the present disclosure includes at least one method according to any one of the nineteenth, twentieth, twenty first, and/or twenty second set of embodiments, wherein said therapeutically effective dose is in the ranges selected from the group consisting of: about 10 mg of said compound per $kg^{-1}$ to about 100 mg of said compound per $kg^{-1}$ of the patient's body weight, about 50 mg of said compound per $kg^{-1}$ to about 100 mg of said compound per $kg^{-1}$ of the patient's body weight, about 100 mg of said compound per $kg^{-1}$ to about 200 mg of said compound per $kg^{-1}$ of the patient's body weight, about 150 mg of said compound per $kg^{-1}$ to about 200 mg of said compound per $kg^{-1}$ of the patient's body weight, about 200 mg of said compound per $kg^{-1}$ to about 300 mg of said compound per $kg^{-1}$ of the patient's body weight, about 250 mg of said compound per $kg^{-1}$ to about 300 mg of said compound per $kg^{-1}$ of the patient's body weight, about 300 mg of said compound per $kg^{-1}$ to about 400 mg of said compound per $kg^{-1}$ of the patient's body weight, about 350 mg of said compound per $kg^{-1}$ to about 400 mg of said compound per $kg^{-1}$ of the patient's body weight, about 400 mg of said compound per $kg^{-1}$ to about 500 mg of said compound per $kg^{-1}$ of the patient's body weight, about 450 mg of said compound per $kg^{-1}$ to about 500 mg of said compound per $kg^{-1}$ of the patient's body weight, about 500 mg of said compound per $kg^{-1}$ to about 1000 mg of said compound per $kg^{-1}$ of the patient's body weight, about 500 mg of said compound per $kg^{-1}$ to about 9000 mg of said compound per $kg^{-1}$ of the patient's body weight, about 500 mg of said compound per $kg^{-1}$ to about 800 mg of said compound per $kg^{-1}$ of the patient's body weight, about 500 mg of said compound per $kg^{-1}$ to about 700 mg of said compound per $kg^{-1}$ of the patient's body weight, about 500 mg of said compound per $kg^{-1}$ to about 600 mg of said compound per $kg^{-1}$ of the patient's body weight, about 600 mg of said compound per $kg^{-1}$ to about 900 mg of said compound per $kg^{-1}$ of the patient's body weight, about 700 mg of said compound per $kg^{-1}$ to about 800 mg of said compound per $kg^{-1}$ of the patient's body weight, about 800 mg of said compound per $kg^{-1}$ to about 1000 mg of said compound per $kg^{-1}$ of the patient's body weight, about 900 mg of said compound per $kg^{-1}$ to about 1000 mg of said compound per $kg^{-1}$ of the patient's body weight.

A twenty-fourth set of embodiments of the invention present disclosure at least one method according to any one of the nineteenth, twentieth, twenty first, twenty second, and/or twenty third sets of embodiments, wherein said dose is selected from the group consisting of: about 10 mg, 20 mg, 30 mg, 40 mg, 50 mg, 100 mg, 150 mg, 200 mg, 250 mg, 300 mg, 350 mg, 400 mg, 450 mg, 500 mg, 600 mg, 700 mg, 800 mg, 900 mg, and 1000 mg of said compound per $kg^{-1}$ of the patient's body weight.

A twenty fifth set of embodiments of the invention present disclosure at least one method according to any one of the nineteenth, twentieth, twenty first, twenty second, and/or twenty third sets of embodiments, wherein said dose is about 50 mg of said compound per $kg^4$ of the patient's body weight. In other embodiment, the dose is about 100 mg of said compound per $kg^{-1}$ of the patient's body weight. In other embodiment, the dose is about 200 mg of said compound per $kg^{-1}$ of the patient's body weight. Still in other embodiment, the dose is about 300 mg of said compound per $kg^{-1}$ of the patient's body weight.

Some of the embodiments, disclosed herein include at least one method for reducing the activity of a protein, comprising the steps of: providing a compound of Formula II or a pharmaceutically acceptable salt or metabolite thereof, wherein said compound of Formula II binds to Replication Protein A or is metabolized into a chemical that binds to Replication Protein A, said compound having the following Formula:

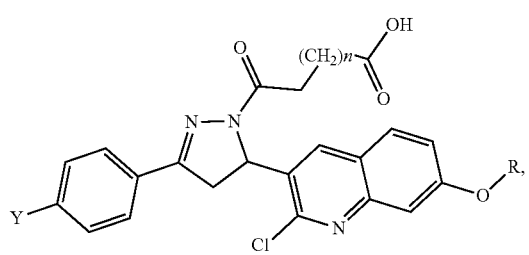

wherein, R is $C_1$-$C_6$ alkyl, Y is a substituent selected from the group consisting of: fluorine, iodine, chlorine, and $F_3CO$, and n is 1, 2, or 3; and contacting said compound of Formula II with at least one isoform of Replication Protein A. In some embodiments, the compound that binds to Replication Protein A is a compound selected from the group consisting of: TDRL-540, TDRL-539, TDRL-551, TDRL-557, TDRL-652, and pharmaceutically acceptable salts and metabolites thereof.

In other embodiments, the compound that binds to Replication Protein A is compound TDRL-551 or a pharmaceutically acceptable salt thereof or a metabolite thereof. In still other embodiments, the contacting step between either said compound of Formula II, or a pharmaceutically acceptable salt or metabolite thereof, and the at least one isoform of Replication Protein A occurs in vivo. In yet still other embodiments, the contacting step between either said compound of Formula II, or a pharmaceutically acceptable salt or metabolite thereof, and the at least one isoform of Replication Protein A occurs in vitro.

Also disclosed is a method of altering eukaryotic cell cycle-progression, comprising the steps of: providing a compound of Formula II, or a pharmaceutically acceptable salt or metabolite thereof, that interferes with eukaryotic cell cycle-progression or that is metabolized into a chemical that interferes with eukaryotic cell cycle-progression, said compound of Formula II having the following Formula:

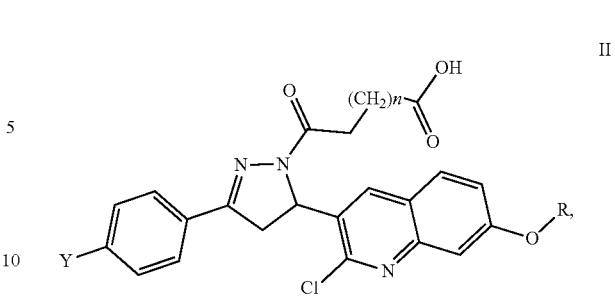

wherein, R is $C_1$-$C_6$ alkyl, Y is a substituent selected from the group consisting of: fluorine, iodine, chlorine, and $F_3CO$, and n is 1, 2, or 3; and contacting said compound of Formula II with at least one eukaryotic cell. In some embodiments, said compound that interferes with eukaryotic cell cycle-progression is a compound selected from the group consisting of: TDRL-540, TDRL-539, TDRL-551, TDRL-557, TDRL-652 and pharmaceutically acceptable salts and metabolites thereof.

In other embodiments, said compound that interferes with eukaryotic cell cycle-progression is compound TDLR-551 or a pharmaceutically acceptable salt thereof or a metabolite thereof. Still in other embodiments, the contacting step between said compound of Formula II, or a pharmaceutically acceptable salt or metabolite thereof, and the eukaryotic cell occurs in vivo. In still other embodiments, the contacting step between said compound of Formula II, or a pharmaceutically acceptable salt or metabolite thereof, and the eukaryotic cell occurs in vitro.

Further disclosed is a method of treating cancer, comprising the steps of: providing a compound of Formula II, or a pharmaceutically acceptable salt thereof, wherein said compound of Formula II interferes with the cell cycle of a cancer cell or is metabolized into a chemical that interferes with the cell cycle of a cancer cell, said compound of Formula II having the following Formula:

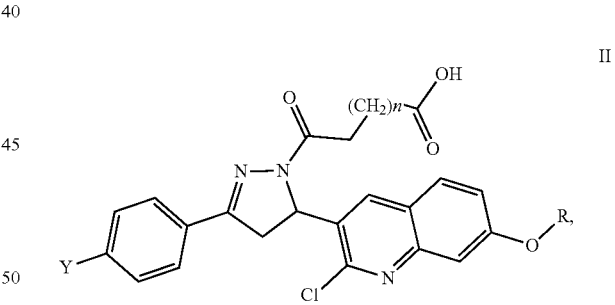

wherein, R is $C_1$-$C_6$ alkyl, Y is a substituent selected from the group consisting of: fluorine, iodine, chlorine, and $F_3CO$, and n is 1, 2, or 3; and contacting said compound of Formula II with at least one cancer cell. In some embodiments, said compound that interferes with the cell cycle of a cancer cell is a compound selected from the group consisting of: TDRL-540, TDRL-539, TDRL-551, TDRL-557, TDRL-652, and pharmaceutically acceptable salts and metabolites thereof.

In other embodiments, said compound that interferes with the cell cycle of a cancer cell is compound TDLR-551 or a pharmaceutically acceptable salt thereof or a metabolite thereof. In still other embodiments, the contacting step between said compound of Formula II, or a pharmaceutically acceptable salt or metabolite thereof, and the cancer cell occurs in vivo. In some embodiments, the contacting step between said compound of Formula II, or a pharmaceutically acceptable salt or metabolite thereof, and the cancer cell occurs in vitro. In still yet some embodiments, the cancer cell is an epithelial ovarian cancer cell or a non-small cell lung cancer cell.

Additionally disclosed is a compound, comprising a compound of Formula:

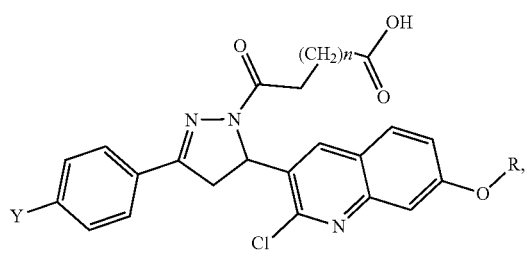

wherein, R is $C_1$-$C_6$ alkyl, Y is a substituent selected from the group consisting of: fluorine, iodine, chlorine, and $F_3CO$, and n is 1, 2, or 3, or a pharmaceutically acceptable salt thereof, or a metabolite thereof. In some embodiments, said compound is a compound selected from the group consisting of: TDRL-540, TDRL-539, TDRL-551, TDRL-557, and TDRL-652 or a pharmaceutically acceptable salt thereof, or a metabolite thereof. In other embodiments, said compound is compound TDLR-551, or a pharmaceutically acceptable salt thereof or a metabolite thereof.

Additionally disclosed is a method of treating a disease, comprising the steps of: supplying at least one compound according to Formula II above or a pharmaceutically acceptable salt or metabolite thereof, wherein said compound is effective for the treatment of at least one disease. In some embodiments, the compound is suitable for administration to a patient. In other embodiments, the compound is suitable for administration to a patient orally. In some exemplary embodiments, the compound is in a formulation and wherein said formulation includes methylcellulose. In yet other embodiments, the compound is suitable for administration to a patient intraperitoneally. In still other embodiments, the compound is in a formulation and wherein said formulation includes Tween-80.

Further disclosed is a method of treating a patient, comprising the steps of: providing at least one compound according to claim 17 or a pharmaceutically acceptable salt or metabolite thereof, wherein said compound is formulated for treatment of a human or an animal patient. In some embodiments, the method further comprises the step of administering at least one dose of the therapeutically effective amount of said compound to a patient. In other embodiments, the patient is also treated with a therapeutically effective dose of at least one compound that damages DNA directly or that inhibits topoisomerase II. Still in some other embodiments, the patient is also treated with a therapeutically effective dose of at least one compound selected from the group consisting of: Cisplatin, Etoposide, Busulfan, Bendamustine, Carboplatin, Carmustine, Chlorambucil, Cisplatin, Cyclophosphamide, Dacarbazine, Daunorubicin, Decitabine, Doxorubicin, Epirubicin, Etoposide, Idarubicin, Ifosfamide, Irinotecan, Lomustine, Mechlorethamine, Melphalan, Mitomycin C, Mitoxantrone, Oxaliplatin, Temozolomide, and Topotecan.

In some embodiments, said dose of Formula II is about 50 mg of said compound per $kg^{-1}$ of the patient's body weight. In other embodiments, said dose of Formula II is about 100 mg of said compound per $kg^{-1}$ of the patient's body weight. Still in other embodiments, said dose of Formula II is about 200 mg of said compound per $kg^{-1}$ of the patient's body weight.

BRIEF DESCRIPTION OF THE FIGURES

FIG. 16 provides structural formulas of TDRL-551 analogs.

DETAILED DESCRIPTION

Figure 1:
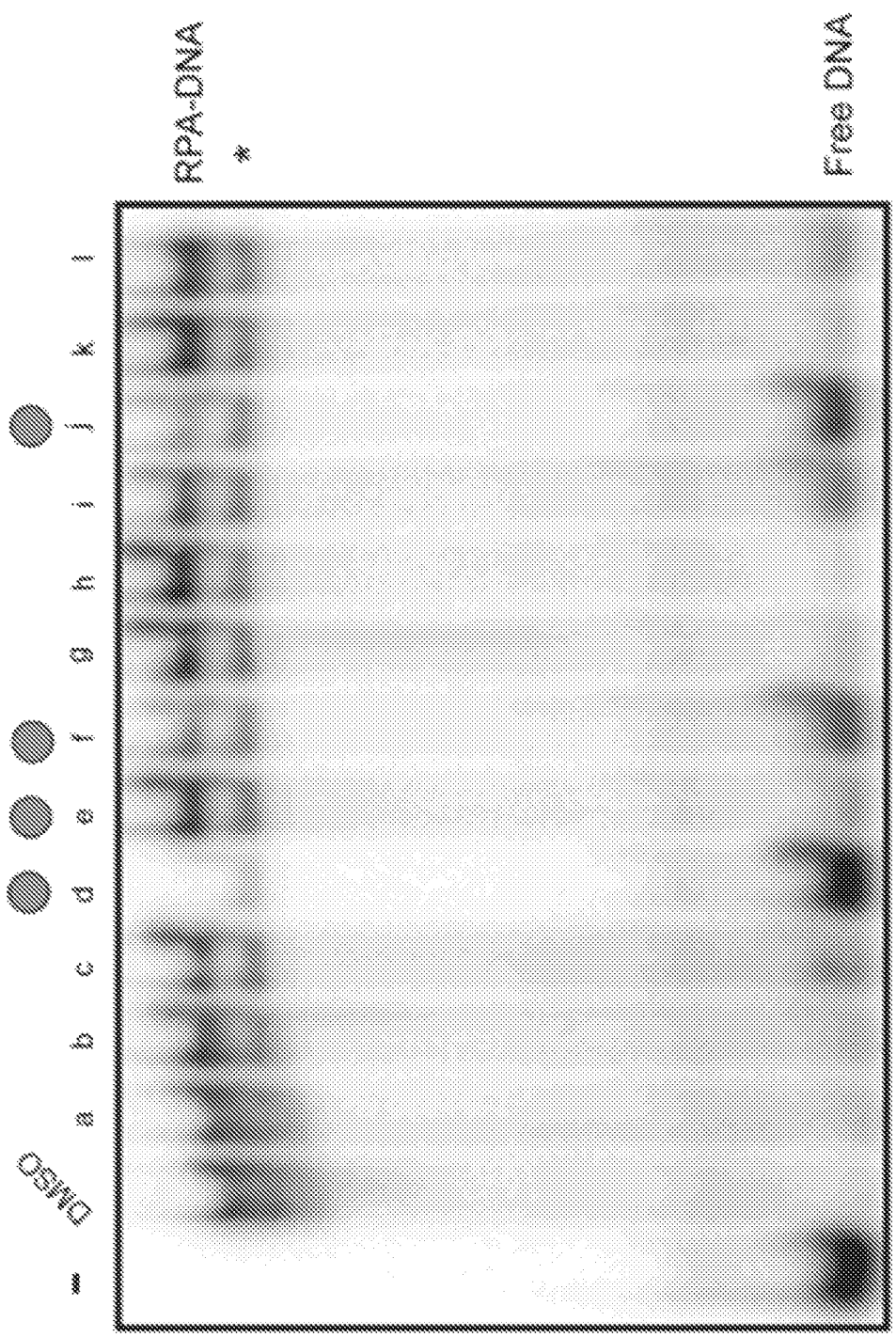
FIG. 1 shows a screen in which 12 TDRL-505 analogs were screened using the Electrophoretic Mobility Shift Assays (EMSA) for RPA-DNA inhibition activity at 100 µM.

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates.

Unless specifically or implicitly stated otherwise the term 'about' as used herein means plus or minus 10 percent. For example, 'about 1.0' encompasses the range of 0.9 to 1.1.

A therapeutically effective amount is an amount of a biologically active compound that has a single or cumulative beneficial effect on the health or well being of a patient.

Inhibiting RPA-DNA interactions has the potential to impact numerous differentially regulated pathways in cancer cells. In DNA replication, RPA inhibition can be used to exploit the highly proliferative nature of cancer cells which is characterized by a large population of cells in S-phase. RPA is also essential for several DNA repair pathways in the cell including nucleotide excision repair (NER). Cisplatin, a common chemotherapeutic used in the treatment of various cancers, induces its cytotoxic effect by forming intrastrand covalent DNA adducts that are repaired primarily by the NER pathway. Consequently, cisplatin treatment, in conjunction with decreased RPA ssDNA binding activity, would be expected to result in decreased efficiency of cellular repair of cisplatin-DNA adducts and increased cytotoxicity. Thus, targeting RPA has the potential not only for single agent activity but also to sensitize cancer cells to therapies that induce DNA damage and genetic instability, such as cisplatin, etoposide and ionizing radiation (IR). Potential therapies include, but are not limited to, Cisplatin, Etoposide, Busulfan, Bendamustine, Carboplatin, Carmustine, Chlorambucil, Cyclophosphamide, Dacarbazine, Daunorubicin, Decitabine, Doxorubicin, Epirubicin, Etoposide, Idarubicin, Ifosfamide, Irinotecan, Lomustine, Mechlorethamine, Melphalan, Mitomycin C, Mitoxantrone, Oxaliplatin, Temozolomide, and Topotecan and the like.

As disclosed herein, small molecules that inhibits the ssDNA binding activity of RPA have been identified. Cellular RPA inhibition results in the inability to enter S phase, induction of cell death and synergistic activity with the chemotherapeutic reagents cisplatin and etoposide. These small molecules which are able to inhibit the ssDNA binding activity of RPA are active both as single agents and in conjunction with commonly used chemotherapeutics for killing cancer cells. In vivo, the compounds can be safely administered up to 200 mg/kg in mice IP and via oral gavage with not signs of overt toxicity and possess anticancer activity versus human non-small cell lung cancer in mouse xenograft model.

Table 1 provides structures of compounds with their corresponding $IC_{50}$ values (μM) calculated from EMSA reactions as described in Experiments and Methods. Compounds were titrated at a range of 1-125 μM.

Some examples of structure-activity relationships ("SAR") identified as areas of interest are highlighted by the shaded ovals in Formula II that follows:

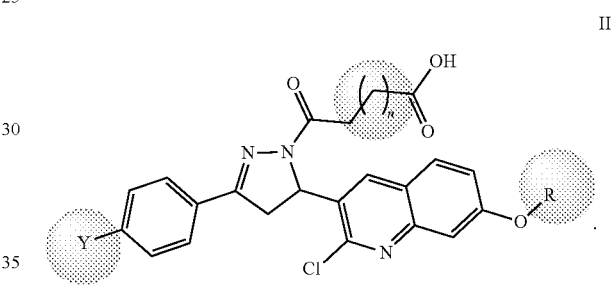

II

Referring now to Table 2, in vitro and cellular $IC_{50}$ values of TDRL-505 and its analogs are shown. The in vitro $IC_{50}$ values are based on EMSA reactions as described in Experiments and Methods. RPA was incubated with the above compounds at a concentration range of 1-125 μM. The cellular $IC_{50}$ values are calculated from clonogenic survival assays as described in Experiments and Methods. The cells were treated with the compounds in Table 2 at a concentration range of 1-200 μM. Four compounds were tested for cellular activity, the rest are indicated with 'na' meaning data not available.

TABLE 1

Structures of compounds with their corresponding $IC_{50}$ values (μM) calculated from EMSA reactions.

| cpd. | STRUCTURE | $IC_{50}$ |
|---|---|---|
| a | 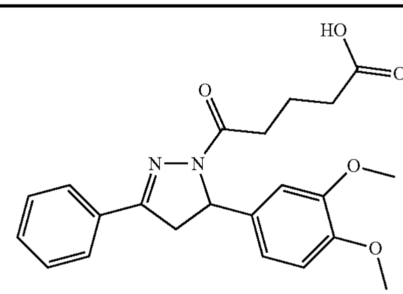 | >100 |

TABLE 1-continued

Structures of compounds with their corresponding IC$_{50}$ values (μM) calculated from EMSA reactions.

| cpd. | STRUCTURE | IC$_{50}$ |
|---|---|---|
| b | 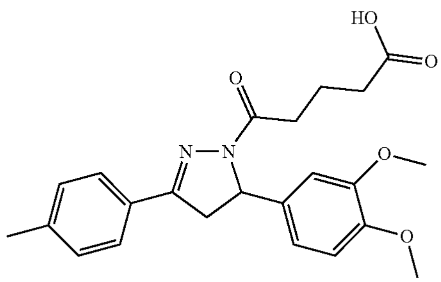 [SMILES: COc1ccc(C2CC(c3ccc(C)cc3)=NN2C(=O)CCCC(=O)O)cc1OC] | >100 |
| c | 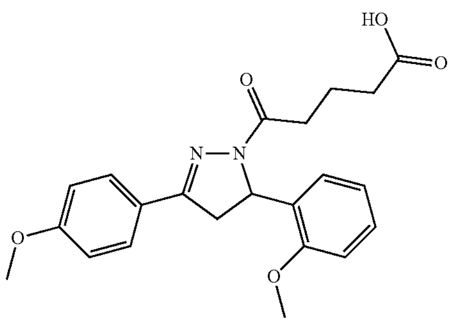 [SMILES: COc1ccc(C2=NN(C(=O)CCCC(=O)O)C(c3ccccc3OC)C2)cc1] | >100 |
| d | 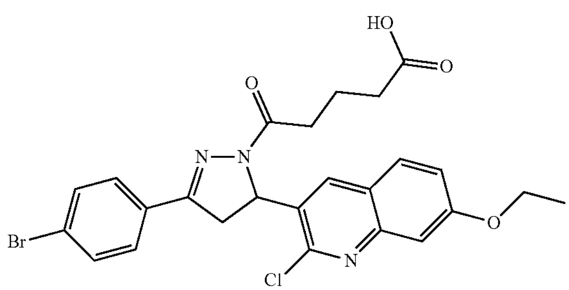 [SMILES: CCOc1ccc2cc(C3CC(c4ccc(Br)cc4)=NN3C(=O)CCCC(=O)O)c(Cl)nc2c1] | 25 |
| e | 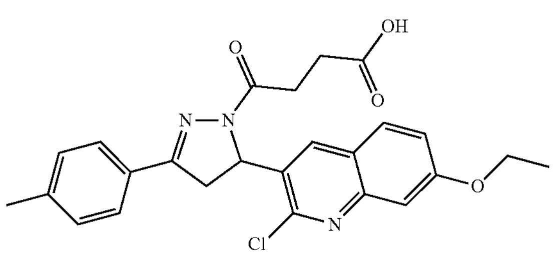 [SMILES: CCOc1ccc2cc(C3CC(c4ccc(C)cc4)=NN3C(=O)CCC(=O)O)c(Cl)nc2c1] | 80 |
| f | 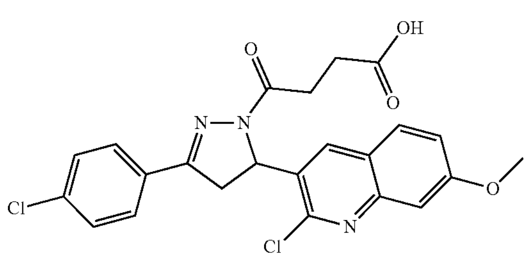 [SMILES: COc1ccc2cc(C3CC(c4ccc(Cl)cc4)=NN3C(=O)CCC(=O)O)c(Cl)nc2c1] | 75 |

TABLE 1-continued

Structures of compounds with their corresponding IC$_{50}$ values (μM) calculated from EMSA reactions.

| cpd. | STRUCTURE | IC$_{50}$ |
|---|---|---|
| g | 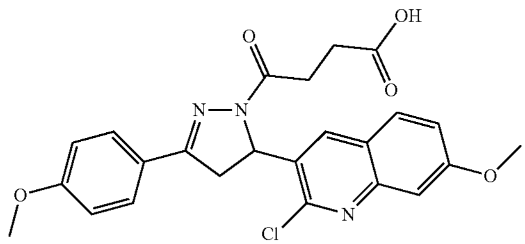 | >100 |
| h | 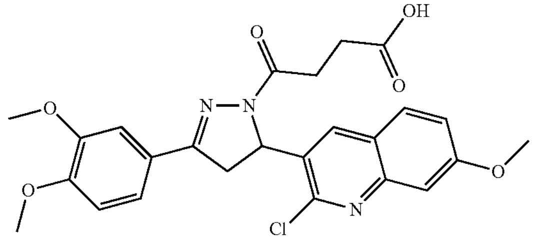 | >100 |
| i | 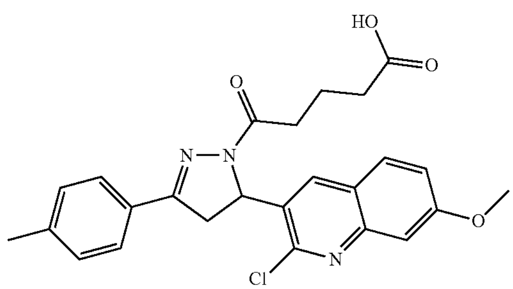 | >100 |
| j | 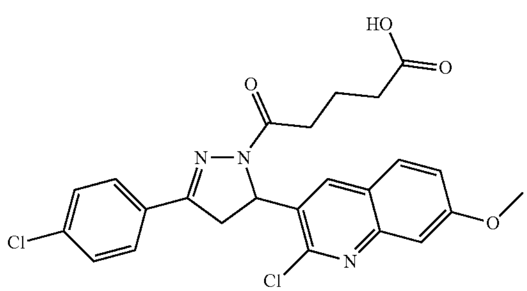 [SMILES: COc1ccc2cc(C3CC(c4ccc(Cl)cc4)=NN3C(=O)CCCC(=O)O)c(Cl)nc2c1] | 60 |
| k | 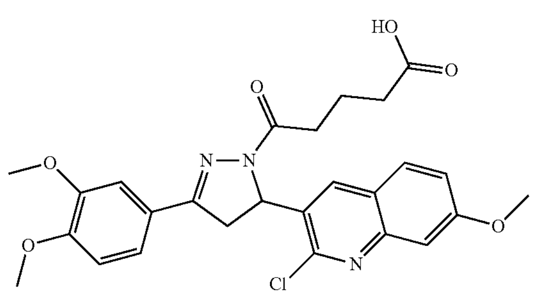 | >100 |

TABLE 1-continued

Structures of compounds with their corresponding IC$_{50}$ values (μM) calculated from EMSA reactions.

| cpd. | STRUCTURE | IC$_{50}$ |
|---|---|---|
| 1 | (structure shown) | >100 |

TABLE 2

In vitro and cellular IC$_{50}$ values of TDRL-505, TDRL-551 and its analogs.

| Entry | Compound | Y | R | n | In vitro IC$_{50}$ (μM) | Cellular IC$_{50}$ (μM) |
|---|---|---|---|---|---|---|
| 1 | TDRL-505 | p-Br | Et | 1 | 38 | >50 |
| 2 | TDRL-533 | p-Br | Me | 1 | >50 | >50 |
| 3 | TDRL-540 | p-F | Me | 1 | >100 | na |
| 4 | TDRL-543 | p-Br | Et | 2 | 25 | 50 |
| 5 | TDRL-539 | p-F | Me | 2 | >100 | na |
| 6 | TDRL-534 | p-Br | Me | 2 | 35 | na |
| 7 | TDRL-556 | p-Br | iPr | 2 | 43 | na |
| 8 | TDRL-551 | p-I | Et | 2 | 18 | 25 |
| 9 | TDRL-557 | p-F$_3$CO | Et | 2 | 30 | na |
| 10 | TDRL-652 | m-I | Et | 2 | 15 | na |
| 11 | TDRL-617 | See below | | | >100 | na |
| 12 | TDRL-634 | See below | | | >100 | na |
| 13 | NG-01-02 | | | | | 75.5 |
| 14 | NG-01-04 | | | | | >100 |
| 15 | NG-01-05 | | | | | na |
| 16 | NG-01-24 | | | | | 7 |
| 17 | NG-01-25 | | | | | 10 |
| 18 | NG-01-07 to 12 [Amine to Acetate] | | | | | na |

The structural formulas of TDRL-551, TDRL-617, and TDRL-634 are shown, respectively, as follows:

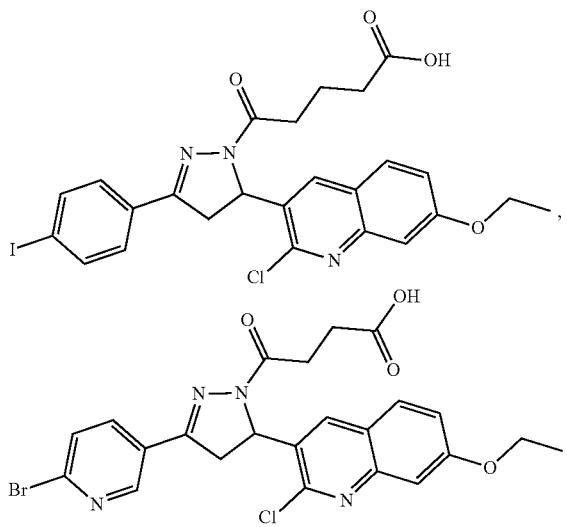

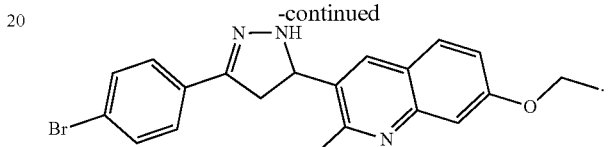

Now referring to FIG. 1, a screen is shown in which 12 TDRL-505 analogs were screened using the EMSA for RPA-DNA inhibition activity at 100 μM. The free DNA and RPA-DNA complexes are indicated. The asterisk indicated the position of the *E. coli* SSB-DNA complex.

Figure 2:
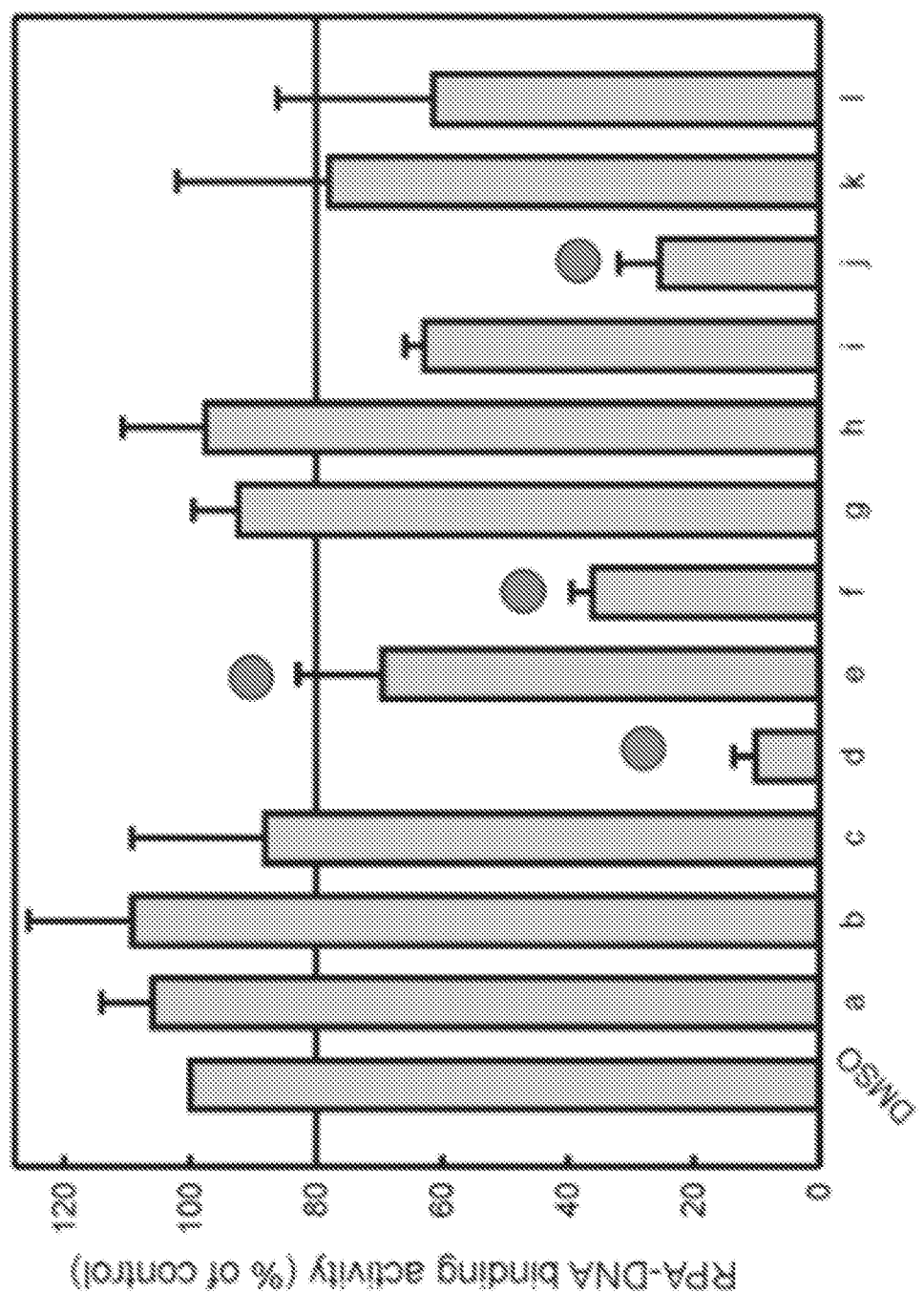
FIG. 2 provides a chart showing quantification of duplicate determinations were averaged and plotted as a percent of control with bars representing the range of values.

Referring now to FIG. 2, a chart is provided showing quantification of duplicate determinations were averaged and plotted as a percent of control with bars representing the range of values.

Figure 3:
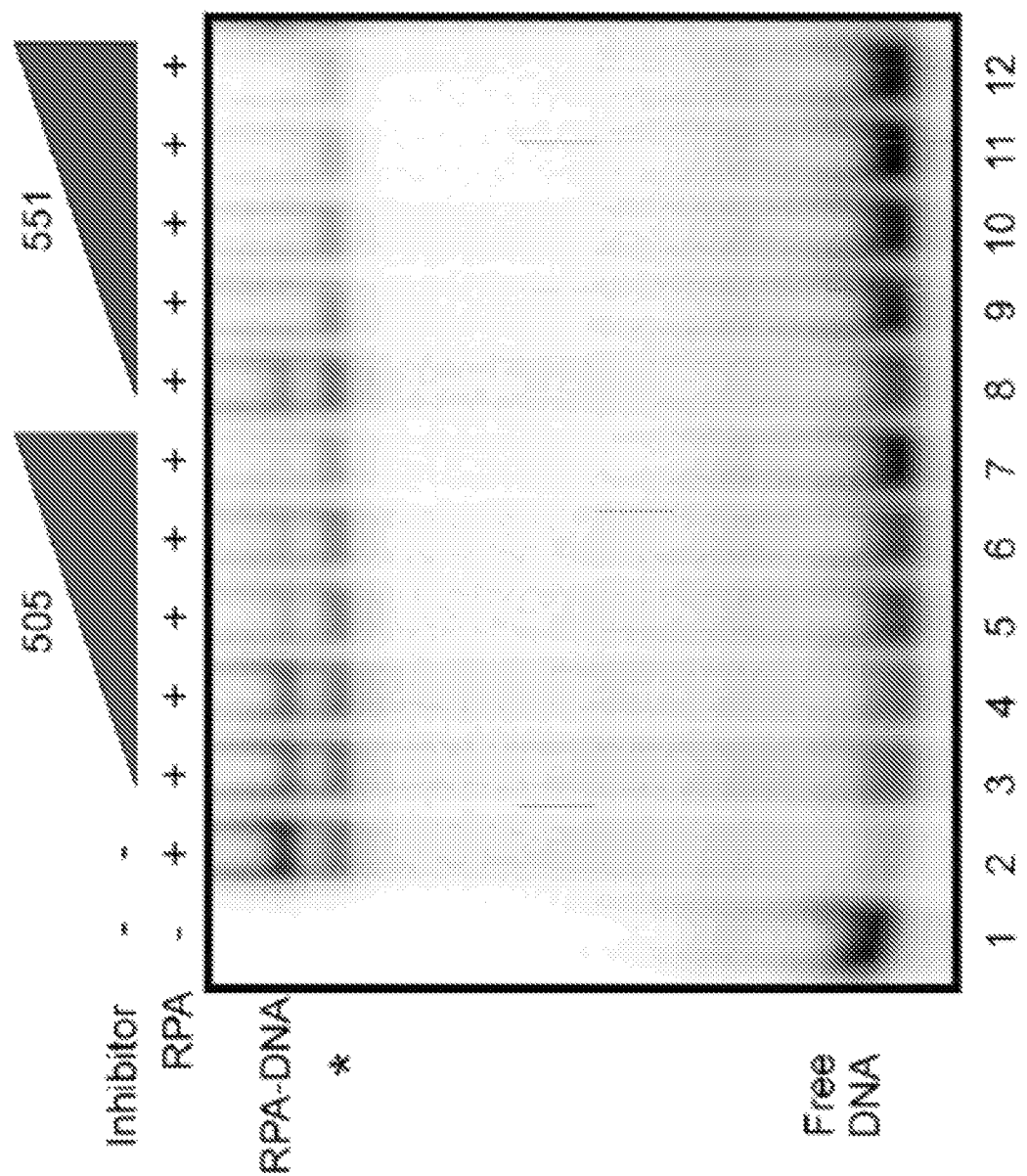
FIG. 3 shows a screen in which RPA was incubated with compounds TDRL-505 and TDRL-551 ranging from 1-125 µM.

Referring now to FIG. 3, a screen is shown in which RPA was incubated with compounds TDRL-505 and TDRL-551 ranging from 1-125 μM. DNA binding was analyzed by EMSA as described in Experiments and Methods. The position of free DNA and the DNA-RPA complex is denoted in FIG. 3. The asterisk indicates the position of the *E. coli* SSB-DNA complex.

Figure 4:
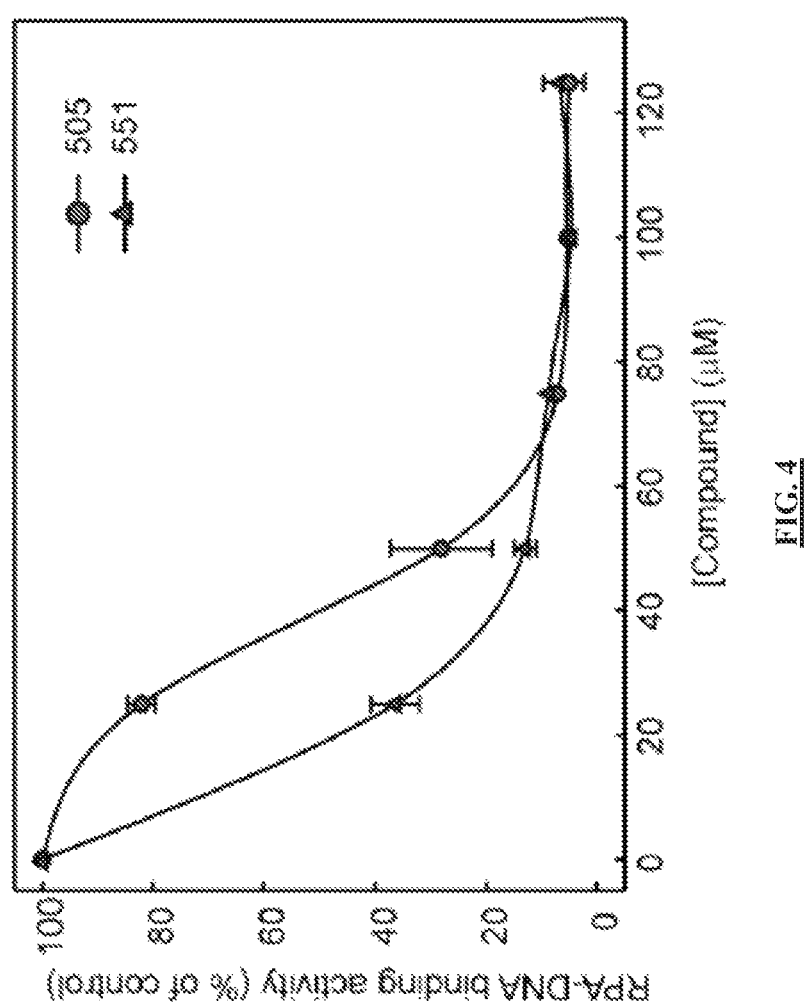
FIG. 4 provides a graph showing quantification of the data presented in FIG. 3.

Referring now to FIG. 4, a graph is provided showing quantification of the data presented in FIG. 3. Data represent the average and standard deviation ("SD") of three independent determinations and the data were fitted using non-linear regression analysis (Sigmaplot) to obtain IC$_{50}$ values.

Figure 5:
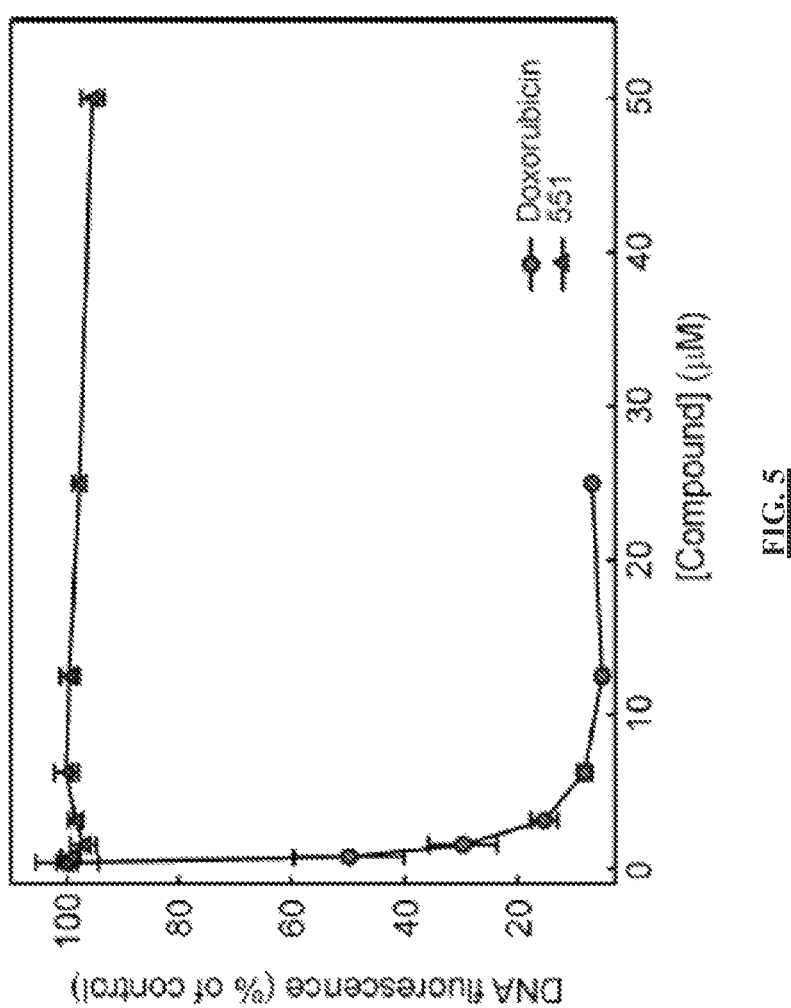
FIG. 5 provides a graph showing fluorescence was measured and data represent the average and SD of three independent determinations.

Referring now to FIG. 5, a graph is provided showing fluorescence was measured and data represent the average and SD of three independent determinations. Fluorescent displacement assays were performed as described herein, and the indicated concentration of 551 or doxorubicin was titrated into reactions containing DNA and SybrGreen. The fluorescence was measured and data represent the average and SD of three independent determinations.

Figure 6:
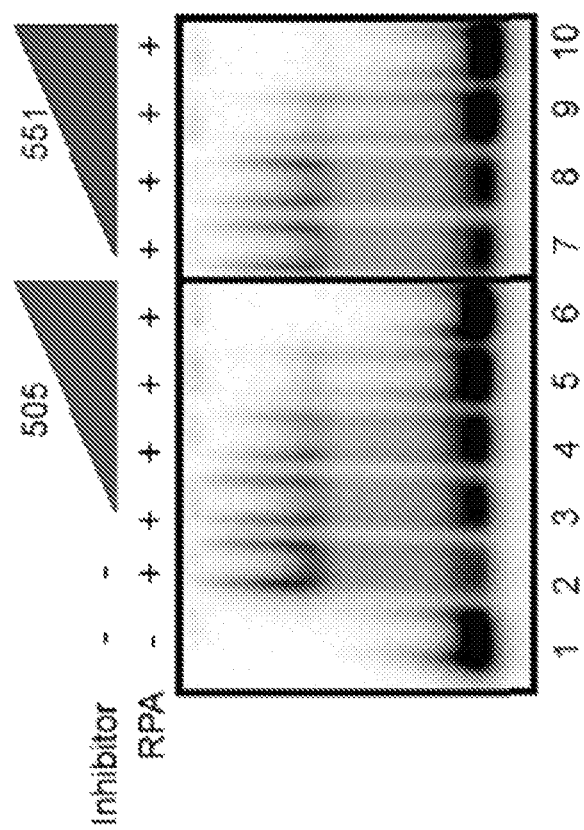
FIG. 6 provides a screen in which RPA-A/B Box was incubated with compounds TDRL-505 and TDRL-551 ranging from 25-100 µM.

Referring now to FIG. 6, a screen is provided in which RPA-A/B Box was incubated with compounds TDRL-505 and TDRL-551 ranging from 25-100 μM. RPA-A/B Box was incubated with compounds TDRL-505 and TDRL-551 ranging from 25-100 μM. DNA binding was analyzed by EMSA as described in Methods. The position of free DNA and the DNA-RPA A/B complex is denoted in the figure.

Figure 7:
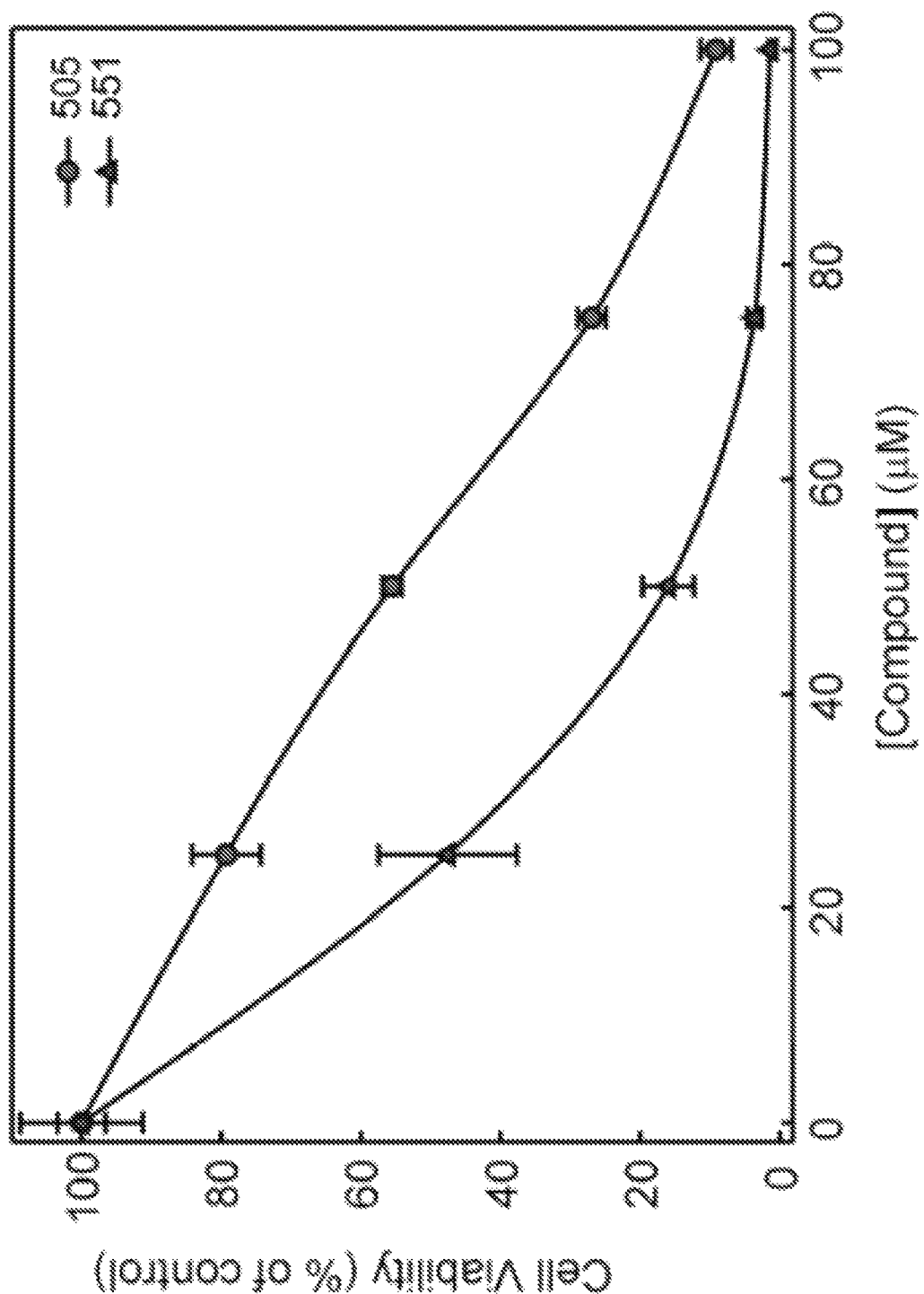
FIG. 7 shows a graph wherein the data represent the average and SEM from three independent determinations and the data were fit using non-linear regression analysis (Sigmaplot) to calculate cellular IC50's.

Referring now to FIG. 7, a graph is shown wherein the data represent the average and SEM from three independent determinations and the data were fit using non-linear regression analysis (Sigmaplot) to calculate cellular IC50's.

A2780 cells were treated with RPA inhibitor TDRL-505 or TDRL-551 for 48 hours and viability was assessed in a colony formation assay as described in Experiments and Methods. The colonies were counted and normalized to the untreated controls to determine cellular viability. The data represent the average and SEM from three independent determinations and the data were fit using non-linear regression analysis (Sigmaplot) to calculate cellular $IC_{50}$s.

Figure 8:
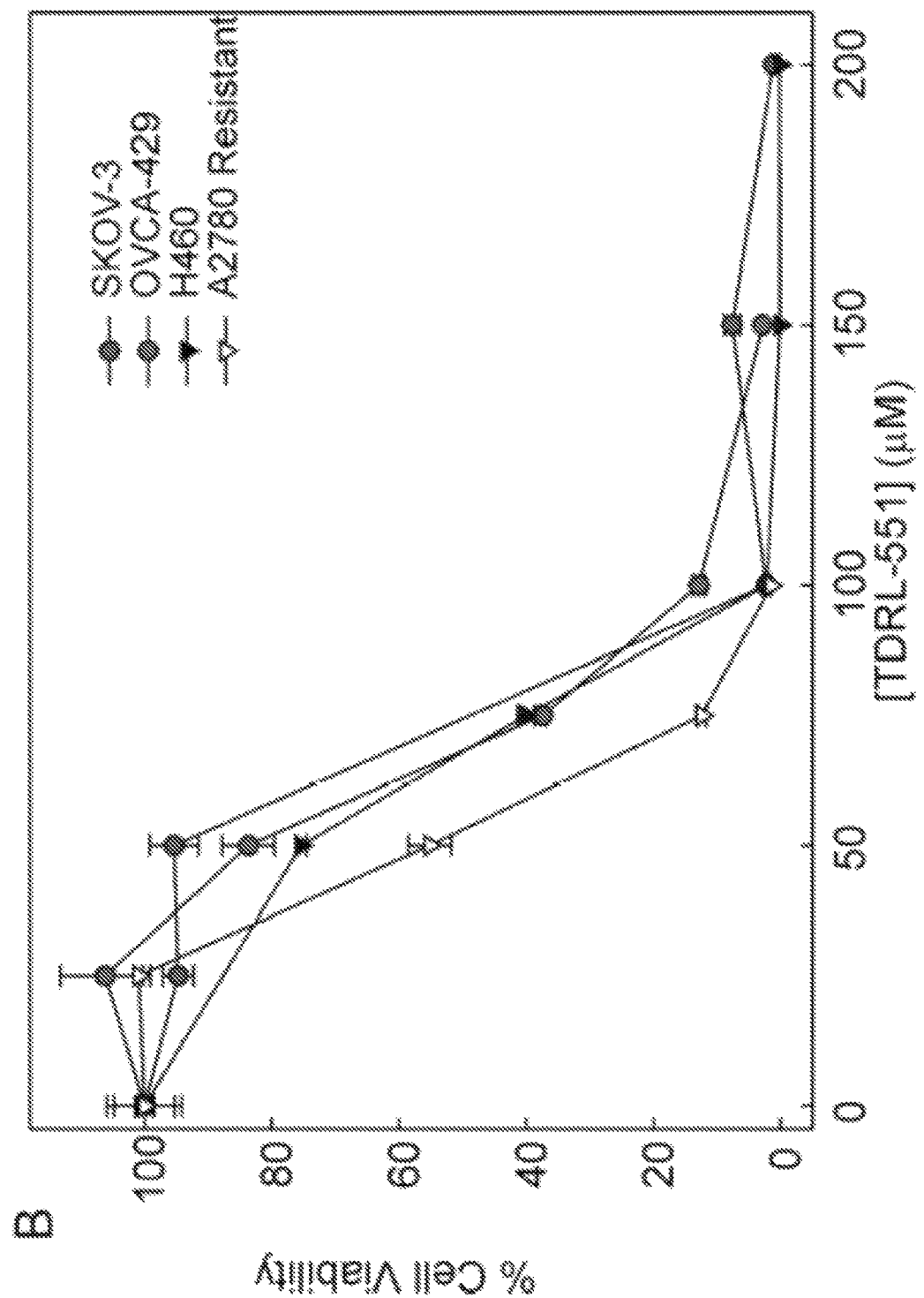
FIG. 8 provides a graph showing the analysis of TDRL-551 single agent activity in H460 NSCLC, SKOV3, A2780/R and OVCA429 EOC cells as shown in FIG. 7.

Referring now to FIG. 8, a graph is provided showing the analysis of TDRL551 single agent activity in H460 NSCLC, SKOV3, A2780/R and OVCA429 EOC cells. Cells were treated with RPA inhibitor TDRL-551 for 48 hours and viability was assessed in a colony formation assay as described in Experiments and Methods. The colonies were counted and normalized to the untreated controls to determine cellular viability. The data represent the average and SEM from three independent determinations and the data were fit using non-linear regression analysis (Sigmaplot) to calculate cellular $IC_{50}$s.

Figure 9:
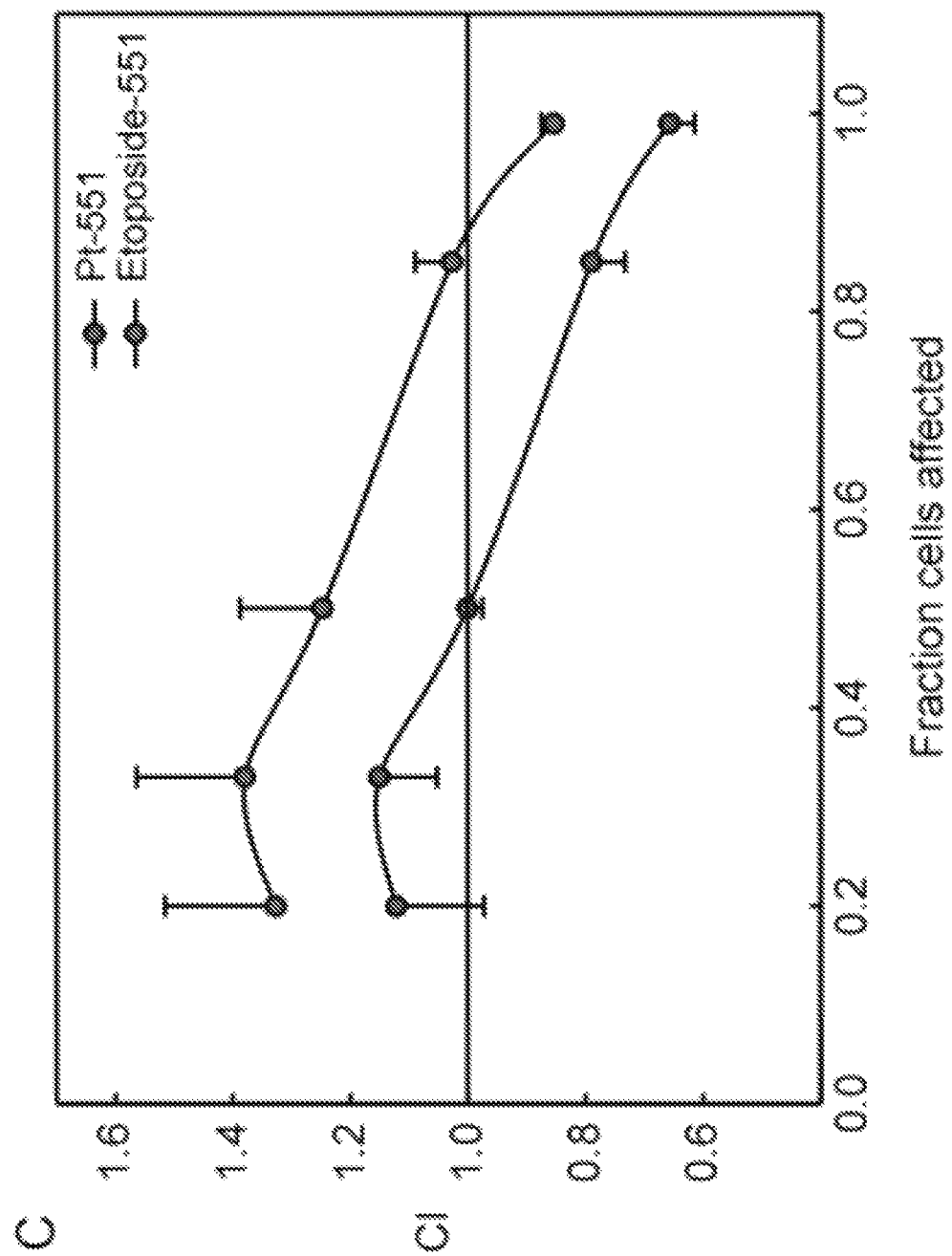
FIG. 9 provides a graph showing the CI of TDRL-551 with Pt and Etoposide were determined through a Chou-Talalay based approach as described in the Experiments section below. The data represent the average and SEM from three independent determinations.

Referring now to FIG. 9, a graph is provided showing the combination index (CI) of TDRL-551 with Pt and Etoposide determined through a Chou-Talalay based approach as described in the Experiments and Methods. The data represent the average and SEM from three independent determinations.

Figure 10:
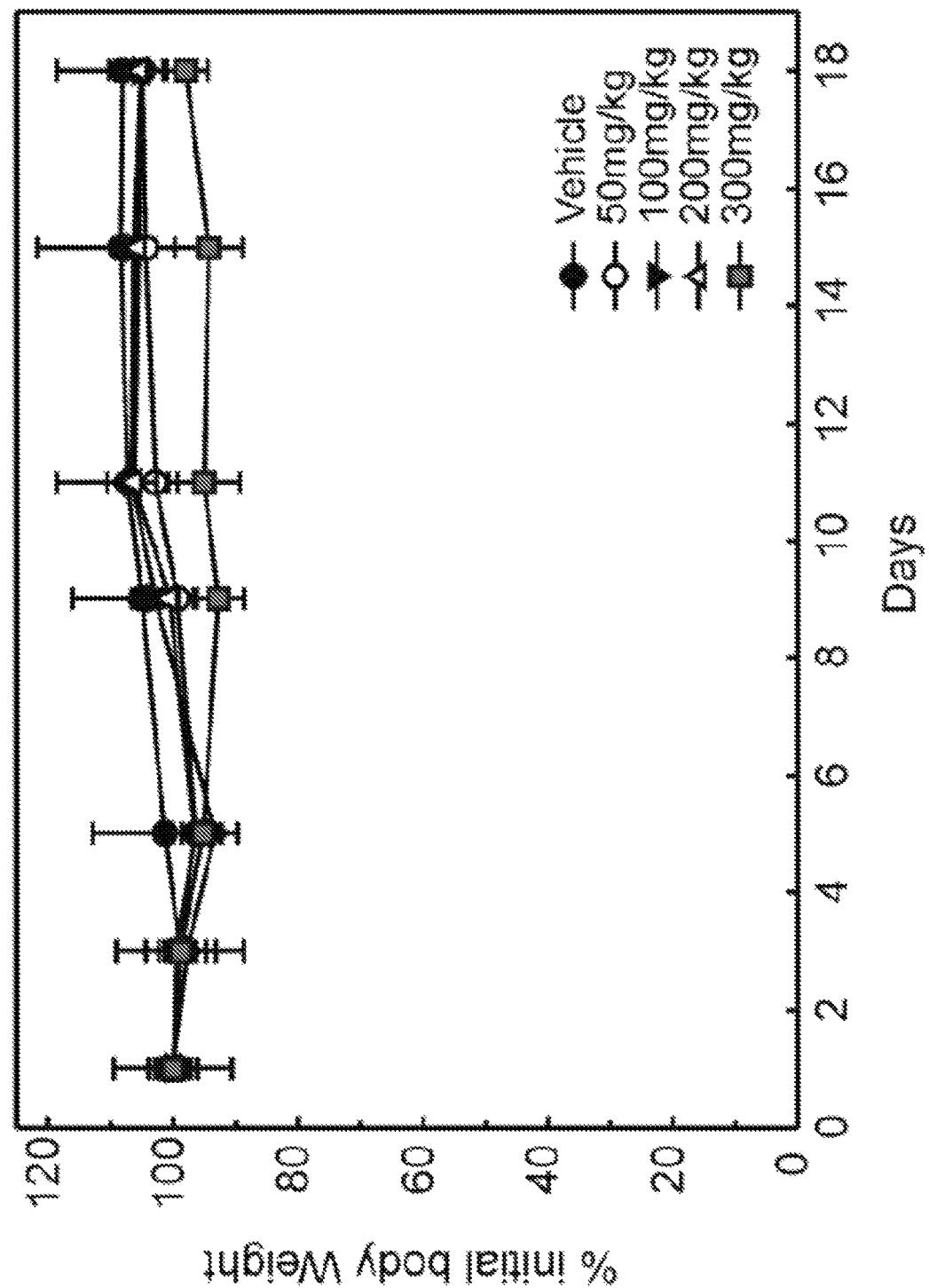
FIG. 10 provides a graph showing acute toxicity and tolerability of TDRL-551 was assessed via body weight determinations following triweekly dosing at the indicated drug concentrations.

Referring now to FIG. 10, a graph is provided showing acute toxicity and tolerability of TDRL-551 were assessed via body weight determinations following triweekly dosing at the indicated drug concentrations. Mice were treated on days 1, 3, 5, 8, 10, and 12 IP as described in Experiments and Methods. Data are reported as the percent of body weight on day 1 and represent the mean±standard error of the mean (n=3).

Figure 11:
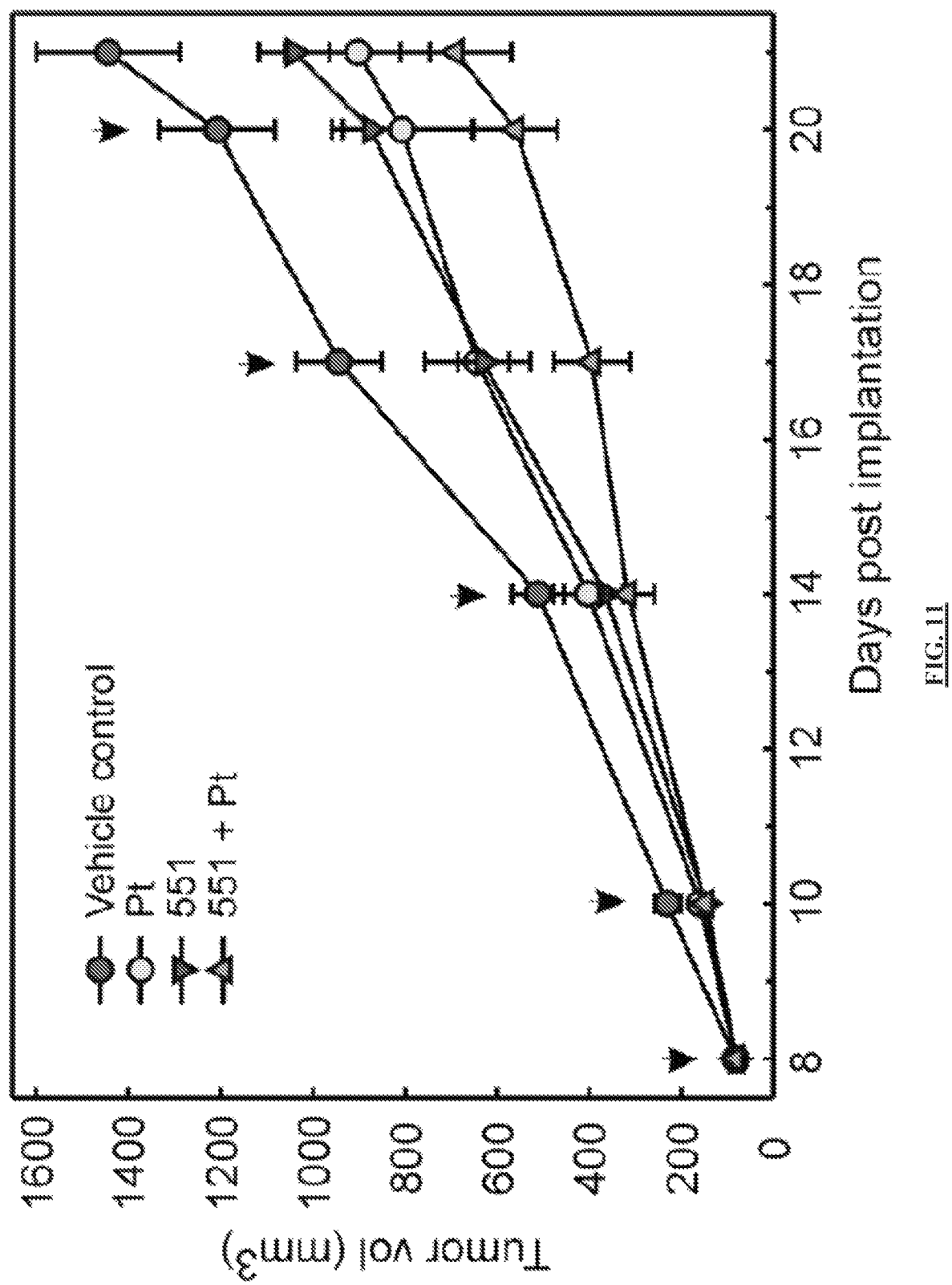
FIG. 11 provides a graph showing in vivo anti-cancer activity was assessed in human H460 NSCLC tumor xenografts in NOD/SCID mice.

Referring now to FIG. 11, a graph is provided showing in vivo anti-cancer activity was assessed in human H460 NSCLC tumor xenografts in NOD/SCID mice. Mice were implanted on day 1, tumor measured by calipers and individual mice randomly assigned to one of 4 treatment arms. Carboplatin was administered once per week on days 8, 14 and 20. TDRL-551 was administered biweekly on days 8, 10, 14, 17, and 20. Tumor volumes were monitored by caliper measurement [tumor volume=length (perpendicular width)$^2$×0.5] biweekly as indicated. Average tumor volume±standard error of the mean for each group is reported in mm$^3$ (n=14).

Figure 12:
FIG. 12 provides a graphical representation of one embodiment of the present disclosure, wherein a small molecule inhibitor targeting RPA can block NER catalyzed repair of cisplatin-DNA damage, HRR and DNA replication, resulting in single agent anti-cancer activity and synergy with Platinum-based therapies.

FIG. 12 provides a graphical representation of one embodiment of the present disclosure, wherein a small molecule inhibitor targeting RPA can block NER catalyzed repair of cisplatin-DNA damage, HRR and DNA replication, resulting in single agent anti-cancer activity and synergy with Platinum-based therapies.

Figure 13:
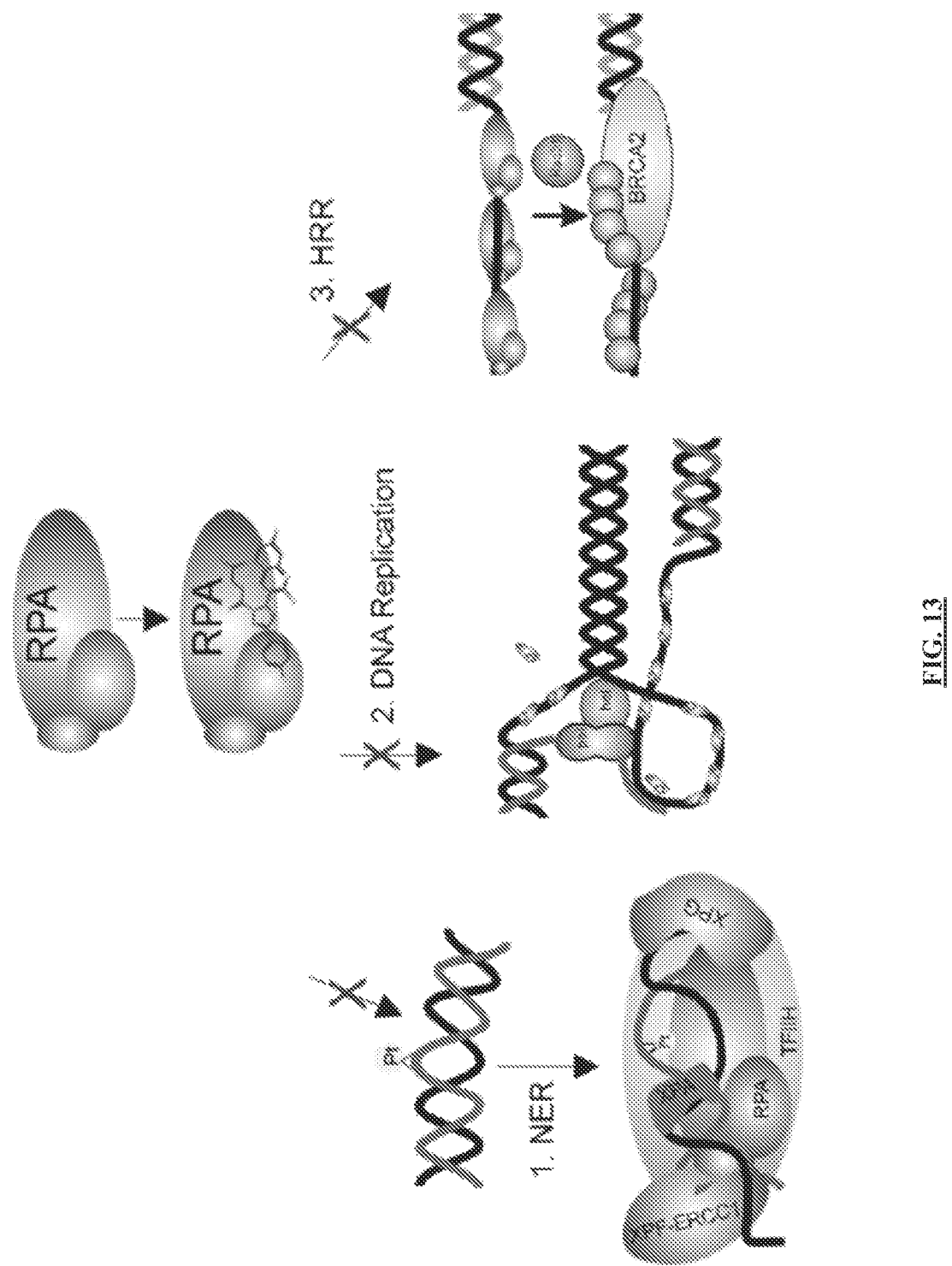
FIG. 13 provides a flow chart showing one embodiment of the present disclosure, wherein a small molecule inhibitor targeting RPA can block NER catalyzed repair of cisplatin-DNA damage, HRR and DNA replication, resulting in single agent anti-cancer activity and synergy with Platinum-based therapies.

FIG. 13 provides a flow chart showing one embodiment of the present disclosure, wherein a small molecule inhibitor targeting RPA can block NER catalyzed repair of cisplatin-DNA damage, HRR and DNA replication, resulting in single agent anti-cancer activity and synergy with Platinum-based therapies.

Experiments

Materials and Methods
Synthesis of TDRL 505 Derivatives

Referring now to Scheme 1. Commercially available ketones such as 1 and aldehydes such as 2 are subjected to a Claisen-Schmidt condensation to create en-ones such as 3 that can be cyclized using reagents such as hydrazine to the generate H1 pyrazoles such as 4. Amide bond chemistry is used with various acids such as 5 in order to modify the N1 position of the pyrazole to form compounds such as the exemplary compound TDRL-505 6.

Scheme 1

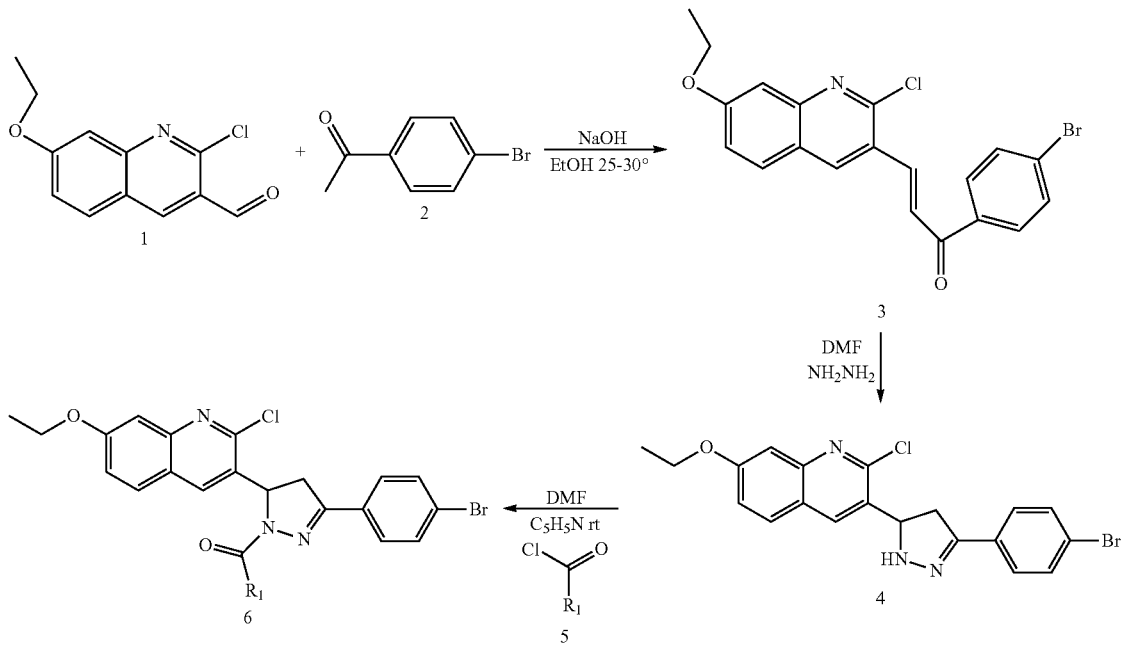

Referring now to Scheme 2. An alternative method for the synthesis of TDRL-505 derivatives is shown below. The reagents and conditions are as follows: (a) N,N-Diisopropylethylamine ("DIEA"), 4-Dimethylaminopyridine ("DMAP"), Dichloromethane ("DCM"), room temperature, 2 h, 90-100%. (b) (i) Dimethylformamide ("DMF"), POCl$_3$, 0° C., 20 min, (ii) Amide, 110° C., 2.5 h, 44-64%. (c) NaOH 10%, EtOH, 45° C., 45 min. (d) H$_2$N—NH$_2$.H$_2$O, EtOH, reflux, 1.5 h, 73-81% (over 2 steps). (e) CHCl$_3$, reflux 1.5 h, 40-72%.

Still referring to Scheme 2, a synthetic approach developed for the preparation of TDRL-505 analogs is depicted in Scheme 2 and involved 5 steps. Quinolines carbaldehydes 4 were prepared by acylation of alkoxyanilines 2 with acetic anhydride 1, followed by Vilsmeier-Haack formylation [Herbert]. Aldol condensation/dehydration with a corresponding methyl ketone 5 and sodium hydroxide yielded enones 6, which, upon treatment with hydrazine, afforded 2-pyrazolines 7. Lastly, acylation at N1 of the pyrazoline core with a cyclic anhydride 8 furnished oxoacids 9. The list of all the synthesized TDRL-505 analogs is shown in Table 2.

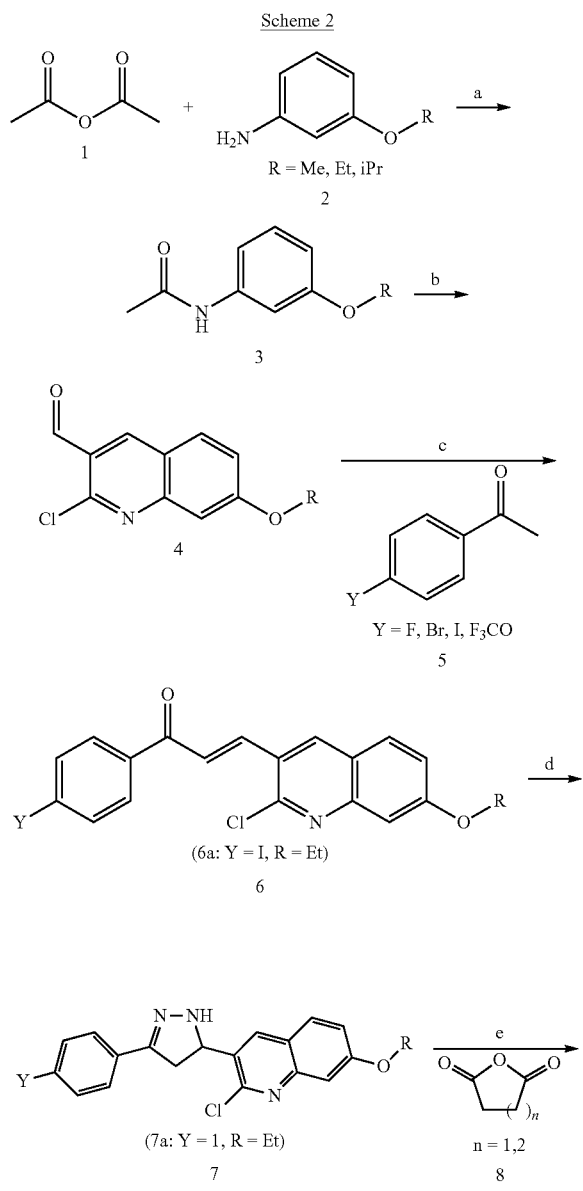

Referring to protein purification, full length, heterotrimeric human RPA (fl-RPA) was expressed in *E. coli* and purified by a three column procedure as previously described (See Patrick S M and Turchi J, Replication Protein A (RPA) Binding to Duplex Cisplatin-damaged DNA Is Mediated through the Generation of Single-stranded DNA. J Biol Chem 1999; 274:14972-8). The DBD-A/B construct was expressed as a SUMO-His$_6$-RPA$^{181\text{-}432}$ fusion protein. *E. coli* BL21 (DE3) cells in log growth were induced for 3 hours with 0.5 mM IPTG at 37° C. The cells were lysed in buffer containing 50 mM Tris pH 7.5, 300 mM NaCl, 10% sucrose, 10 mM imidazole, 25 µg/ml lysozyme, 1 µg/ml leupeptin, 1 µg/ml pepstatin and 0.5 mM PMSF. The lysate was loaded onto a Ni-NTA column washed and then incubated overnight with wash buffer containing 3 µg/ml ULP1 protease to cleave the SUMO tag. The cleaved His$_6$-RPA$^{181\text{-}432}$ was eluted from the Ni-NTA column with elution buffer containing 350 mM imidazole. The His6-RPA was then further purified on a size exclusion column (SEC) to remove the cleaved SUMO tag fragment. The SEC pool was then concentrated and stored at −80° C.

Referring now to Electrophoretic Mobility Shift Assays ("EMSA"), EMSA reactions (20 µL) were performed with 50 nM fl-RPA and 2.5 nM 5'[$^{32}$P]-labeled 34-base DNA in buffer containing 20 mM HEPES (pH 7.0), 1 mM DTT, 0.001% NP-40, 100 mM NaCl, 5 mM MgCl$_2$ and 50 µg/ml bovine serum albumin (BSA). Chemical compounds, either purchased from ChemDiv or synthesized in the laboratory, were suspended in DMSO and titrated as detailed in each figure. The DMSO concentration in the reaction mixture was kept constant at or below 5%. RPA was incubated with inhibitor or DMSO control in reaction buffer for 30 minutes before the addition of DNA. Reactions were incubated for 5 minutes at room temperature and products separated via 6% native polyacrylamide gel electrophoresis. The bound and unbound fractions were then quantified by phosphor-imager analysis using ImageQuant software (Molecular Dynamics, CA) and IC$_{50}$ values calculated by non-linear regression using SigmPlot (Sysat). For EMSA reactions with RPA DBD-A/B, 150 nM DBD-A/B was used and electrophoresis was performed at 4° C. All other conditions were identical to those described for the full length RPA.

Referring now to chemical synthesis, all solvents and chemicals were used as purchased from commercial suppliers. $^1$H NMR spectra were obtained on a Bruker Avance III 500 MHz NMR spectrometer. Chemical shifts are expressed in parts per million (ppm, δ), relative to tetramethylsilane (TMS) as internal reference. Signals are described as s (singlet), d (doublet), dd (doublet of doublets), dt (doubles of triplets), t (triplet), q (quartet), orp (pentet).

For 2-chloro-7-ethoxy-3-(3-(4-iodophenyl)-4,5-dihydro-1H-pyrazol-5-yl)quinoline (7a), NaOH (0.83 mL, 2.5 M in water, 2.07 mmol) was added dropwise to a solution of 4-iodoacetophenone (0.36 g, 1.47 mmol) and 2-chloro-7-ethoxyquinoline-3-carbaldehyde (0.35 g, 1.47 mmol) in EtOH (12 mL). After stirring for a 45 min at 40° C., the reaction mixture was quenched with HCl (1.38 mL, 3 M). The crude mixture containing the resulting enone was then filtered, thoroughly washed with EtOH, and used in the next step without further purification. Hydrazine monohydrate (0.36 mL, 7.33 mmol) was added dropwise to a suspension of the enone obtained in the previous step in EtOH (30 mL). The mixture was refluxed for 1.5 h with stirring, after which it was allowed to cool to room temperature. The obtained solid was filtered and washed with EtOH. Further purification by trituration with EtOH furnished the title compound as an off-white solid (0.57 g, 81% over 2 steps). $^1$H NMR (500 MHz, DMSO-$d_6$) δ1.41 (t, J=7.0 Hz, 3H), 2.89 (dd, J=16.5, 10.0 Hz, 1H), 3.67 (dd, J=16.5, 11.0 Hz, 1H), 4.20 (q, J=7.0 Hz, 2H), 5.19 (dt, J=10.5, 3.5 Hz, 1H), 7.27 (dd, J=9.0, 2.5 Hz, 1H), 7.34 (d, J=2.5 Hz, 1H), 7.44 (d, J=8.5 Hz, 2H), 7.74 (d, J=8.5 Hz, 2H), 7.84 (d, J=3.5 Hz, 1H), 7.97 (d, J=9.0 Hz, 1H), 8.42 (s, 1H).

For 4-(5-(2-chloro-7-ethoxyquinolin-3-yl)-3-(4-iodophenyl)-4,5-dihydro-1H-pyrazol-1-yl)-4-oxobutanoic acid (9a or TDRL-551), a round-bottom flask coupled with a reflux condenser and containing a dry mixture of 2-chloro-7-ethoxy-3-(3-(4-iodophenyl)-4,5-dihydro-1H-pyrazol-5-yl) quinoline (7a) (0.6 g, 1.25 mmol) and glutaric anhydride (0.14 g, 1.25 mmol) was immersed into a preheated oil bath (65° C.). CHCl$_3$ (24 mL) was then added through the condenser in one portion. The resulting solution was refluxed for 1.5 h with stirring, after which it was allowed to cool to room temperature. The obtained solid was filtered and washed with ethyl acetate. Further purification by trituration with ethyl acetate yielded acid 9a as an off-white solid (0.53 g, 72%). $^1$H NMR (500 MHz, DMSO-$d_6$) δ1.40 (t, J=7.0 Hz, 3H), 1.83 (p, J=7.5 Hz, 2H), 2.30 (t, J=7.5 Hz, 2H), 2.82 (dt, J=15.0, 7.5 Hz, 1H), 2.91 (dt, J=15.0, 7.5 Hz, 1H), 3.28 (dd, J=18.0, 5.5 Hz, 1H), 3.97 (dd, J=18.0, 12.0 Hz, 1H), 4.19 (q, J=7.0 Hz, 2H), 5.83 (dd, J=12.0, 5.5 Hz, 1H), 7.26 (dd, J=9.0, 2.5 Hz, 1H), 7.35 (d, J=2.5 Hz, 1H), 7.57 (d, J=8.5 Hz, 2H), 7.84 (d, J=8.5 Hz, 2H), 7.93 (d, J=9.0 Hz, 1H), 7.99 (s, 1H), 12.09 (s, 1H).

Referring now to cell culture, A2780 cells and A2780/R cells were purchased from Sigma. All other cell lines were from ATCC and routinely tested for mycoplasma contamination. Cells were maintained in RPMI media supplemented with 10% FBS (Atlanta Biological), penicillin and streptomycin. Cultures were incubated at 37° C. in 5% CO$_2$ and sub-cultured 2-3 times per week.

Referring now to clonogenic survival assays, cells were plated in a 6 well (100,000 cells/well) or 24 well (25,000 cells/well) plate, incubated for at least 18 hours and then treated with Pt/etoposide and/or RPA inhibitors. After 48 hours of treatment, the cells were re-plated in 10 cm dishes (500-1000 cells/dish) and incubated for 8-10 days to allow colony formation. Plates were then washed with PBS, fixed with glutaraldehyde (Fisher Scientific) and stained with crystal violet (Acros Organics). The colonies were then counted using an Acolyte Synbiosis colony counter, viability determined versus vehicle controls which were plotted versus drug concentration.

Referring now to Assessment of Synergy via Combination Index, in the combination index studies, the A2780 cells were treated with RPA inhibitor and Pt/etoposide alone as well as the combination of both—the inhibitor and the DNA damaging chemotherapeutic agent. The range of treatment was dependent on the IC$_{50}$ of each inhibitor/drug. If the IC$_{50}$ was X, then the cells were treated at a range of X/4 to 3X concentration in a colony formation assay. The kill curves from both the single agent treatments as well as the combination treatment were used in a Chou-Talalay based method to determine the combination index (CI) at different fractions of cells affected (See Chou T C, Drug combination studies and their synergy quantification using the Chou-Talalay method. Cancer Res 2010; 70:440-6 and Chou T C, Talalay P., Quantitative-analysis of dose-effect relationships—the combined effects of multiple-drugs or enzyme-inhibitors. Advances in Enzyme Regulation 1984; 22:27-55). A CI>1 indicates antagonism between the two agents, while a CI<1 indicates synergy. A CI of 1 demonstrates an additive effect.

Referring now to compound-DNA binding assay, a competitive DNA intercalation assay was performed using SYBR-Green (Sigma) and salmon sperm DNA (Fisher). Reactions were carried out in 25 mM MOPS (pH 6.5) containing 30 μM sonicated salmon sperm DNA, SYBR-Green and varying concentrations of RPA inhibitors. Reactions were performed in a black 96-well plate in a final volume of 110 μl. Doxorubicin, a known non-covalent DNA binding chemotherapeutic, was used as a positive control. Fluorescence was measured using a BioTek® Synergy™ H1 hybrid multi-mode microplate reader with an excitation wavelength of 485 nm, emission wavelength of 528 nm and a read height of 7 mm. Data were collected using BioTek® Gen5™ reader software. Reactions were incubated a maximum of 5 minutes before measurements were collected.

Referring now to in vivo analysis of TDRL-551, non-obese diabetic/severe combined immunodeficient mice (NOD/SCID) were obtained from The Jackson Laboratory. All animal studies were conducted under the guidelines of the NIH and were approved by the Institutional Animal Care and Use Committee of Indiana University School of Medicine. Animals were maintained under pathogen-free conditions and a 12-hour light-dark cycle. The safety and tolerability of TDRL-551 was assessed in naïve NOD/SCID mice. Mice were treated IP with increasing concentrations of TDRL-551 in a formulation consisting of 20% DMSO, 10% Tween 80, 70% PBS. Based on preliminary PK analysis and a half-life of ~7 hours (data not shown) we administered 3 doses per week for two weeks and measured body weight every other day.

To assess anti-cancer efficacy, the hind flanks of sixty 8-10 week old mice were implanted with 2×10$^6$ H460 NSCLC cells in matrigel. Tumor volumes were monitored by caliper measurement [tumor volumes=length×(perpendicular width)$^2$×0.5]. Mice with tumors ranging between 32-152.5 mm$^3$ 8 days following implantation were randomized into 4 treatment arms. Carboplatin was dissolved in water and administered via intraperitoneal injection at 50 mg/kg on days 8, 14, and 20 following implantation. TDRL-551 was suspended in 20% DMSO, 10% Tween 80, 70% PBS and administered via intraperitoneal injection at 200 mg/kg biweekly on days 8, 10, 14, 17, and 20. Vehicle controls were administered to arms not receiving indicated treatments. Tumor volumes were monitored biweekly as indicated and the results are presented as the average tumor volume±standard error of the mean for each group (n=14 per group).

Referring now to certain results obtained from screening TDRL-505 analogs, with a goal, in one embodiment, of improving the potency and physiochemical properties of TDRL-505, 26 analogous compounds were screened to assess their ability to inhibit RPA-DNA binding activity. These 26 compounds shared the same 2-pyrazoline core structure as TDRL-505, but differed in either the type/length of the side chain attached to N1, the substitution of the phenyl group at C3, or the type of aromatic ring at C5. Data from a representative of 12 compounds are shown in FIG. 1 along with quantification of the data in FIG. 2. Each of the analogs that displayed inhibitory activity towards RPA was titrated over a range of concentrations to determine $IC_{50}$ values (shown above in Table 1). These data were used to determine SAR. Some important aspects of the molecules were identified: the length of the carboxylic acid chain, the halogen on the phenyl ring, and the alkyl ether in the quinoline ring (Formula I above). Consequently, an organic synthesis scheme was pursued to prepare additional TDRL-505 analogs and further interrogate the structure activity relationships.

Referring now to in vitro inhibition of RPA's DNA binding activity, the in vitro inhibition of RPA's DNA binding activity was determined by titrating all synthesized TDRL-505 analogs over a range of concentrations from 0-125 µM in an EMSA based assay (Table 2). A slight increased potency was observed by addition of a methylene group to the oxocarboxylic acid moiety (entries 1 and 4, and 2 and 6). Additionally, a correlation was found between the identity of the halogen atom on the phenyl ring and the effectiveness of the compound. Iodine imparted good inhibitory activity, followed by bromine, chlorine and fluorine, in that order (entries 2 and 3, 4 and 8, and 5 and 6). The pattern of halo-substitution on the phenyl ring was also evaluated. Since the meta-iodo isomer did not exhibit any effect over its para analog (entries 8 and 10), we pursued the latter due to its simpler purification process. Lastly, a fluorinated substituent, the trifluoromethoxy group, did not alter the potency of the compound when compared to the parental bromo substitution (entries 4 and 9). Another part of the molecule that was subject of analysis was the alkyl ether moiety on the quinoline ring. The replacement of the ethyl group by either a methyl or isopropyl counterpart resulted in a slight decrease in inhibitory activity (entries 1 and 2, and 4, 6 and 7). Of all analogs tested, TDRL-551 (entry 8) exhibited the highest in vitro, as well as cellular, activity.

To further interrogate the most potent compound TDRL-551, its activity was directly compared to that of the parent compound, TDRL-505. The data presented in FIG. 3 compare the EMSA based in vitro inhibitory activity of TDRL-551 with that of TDRL-505. The $IC_{50}$ values, calculated form the plotted graphs (FIG. 4), were found to be 18 and 38 µM, respectively, making TDRL-551 greater than twice as potent than its predecessor. The two potential mechanisms for inhibition are either a direct interaction with the protein or an interaction with the DNA that renders it unable to bind to the protein. Previous in silico docking analyses suggested that the 505 class of compounds inhibits DNA binding activity via a direct interaction with the protein RPA. To confirm the mechanism of inhibition for 551 was via an interaction with RPA and not DNA the ability of TDRL-551 to bind to DNA was assessed using a fluorescence displacement assay. The results presented in FIG. 5 demonstrate that no DNA binding activity was observed for 551 and confirm that the compound inhibits the protein-DNA interaction by binding directly to the RPA protein and not via binding to the DNA. To further delve into the mechanism of binding, it was tested whether TDRL-551 could inhibit RPA DBD-A/B binding (the major high affinity DNA binding core) to DNA. Both TDRL-551 and TDRL-505 inhibit RPA DBD-A/B-DNA interaction and hence employ a similar inhibition mechanism (FIG. 6).

Referring now to cellular activity of TDRL-551, specifically single agent anti-cancer activity of RPA inhibitors in EOC cell line, considering the essential role of RPA in S-phase DNA replication and previous data with both reversible and irreversible RPA inhibitors, the TDRL-505 analogs were evaluated for single agent anti-cancer activity in the A2780 EOC cell line using clonogenic survival assays (Table 2). Consistent with in vitro EMSA based studies, TDRL-551 showed the best single agent activity in these cells. Also in line with the in vitro results was the relative cellular inhibitory activity of all tested compounds. FIG. 7 shows the data obtained from clonogenic survival assays, comparing the single agent activity of the original lead TDRL-505 and the optimized lead, TDRL-551. TDRL-505's $IC_{50}$ was found to be 55 µM, while TDRL-551 was twice as potent with an $IC_{50}$ of 25 µM. Surprisingly, the degree of improvement in potency remained consistent between the in vitro and cellular assays. To ensure that the activity was not cell line specific, the single agent activity of TDRL-551 was assessed in three other EOC cell lines, SKOV3 and OVCA429 (ATCC) both of which were isolated from patients with recurrent ovarian cancer following platinum therapy and the cisplatin resistant A2780 derivative. Also assessed was activity in the H460 NSCLC cell line. In each case, TDRL-551 displayed single agent activity similar to that observed in the parental A2780 EOC cells (FIG. 8) demonstrating that, as would be expected for an RPA inhibitor, the mode of activity is not restricted to a single cell line or cancer type.

Referring now to synergy with DNA damaging chemotherapeutic agents in EOC, since repair and tolerance of Pt-DNA lesions predominantly occur via NER and HR, cellular inhibition of RPA should have a dramatic effect on the sensitization of cancer cells to Pt. In order to determine whether inhibition of RPA with TDRL-551 synergizes with Pt in EOC cells, combination treatment studies were performed with TDRL-551 and cisplatin. The platinum sensitive A2780 cell line was used as the cell culture model for EOC. FIG. 9 shows an average of three biological replicate experiments for combination studies of TDRL-551 with Pt in A2780 cell line with appropriate single agent controls. The data show a synergistic effect indicated by a CI<1 at 0.5 or higher fraction of cells affected. The data obtained are consistent with the hypothesis that RPA inhibition makes cancer cells more sensitive towards Pt and hence acts synergistically with cisplatin treatment. Since RPA also plays a crucial role in replication, also tested was TDRL-551 in combination with etoposide, a topoisomerase II inhibitor. TDRL-551 was synergistic with etoposide at the highest fraction of cells affected (>0.8) (FIG. 9).

RPA Inhibitor TDRL-551 displays single agent anti-cancer activity and sensitizes NSCLC tumors to platinum based treatment in vivo. To determine the effect of RPA inhibition via TDRL-551 treatment in vivo first assessed was tolerability, and experiments demonstrated a good safety profile with no weight loss observed with intraperitoneal administration up to 200 mg/kg (FIG. 10). A slight decrease in body weight was observed at 300 mg/kg, but still did not reach greater than 10% loss of weight. Co-treatment with carboplatin was also assessed and again, no adverse effects or loss of weight was observed up to 200 mg/kg. Anti-cancer activity in H460 NSCLC xenografts was then determined.

Initial pharmacokinetic analysis revealed the ability to achieve a plasma concentration of >20 µM with a half-life of over 7 hours. Tumor cells were therefore implanted in NOD/SCID mice that were randomized and treated with vehicle, TDRL-551; carboplatin; or the combination of TDRL-551 and carboplatin (FIG. 11). Carboplatin is often used in the treatment of NSCLC and forms DNA adducts chemically indistinguishable from those forms with cisplatin. As a result of the similarity in the DNA adducts formed between carboplatin and cisplatin, the repair pathways that impact sensitivity are identical. Tumor volumes were monitored for 2 weeks following initiation of treatment regimens and averages for each treatment arm are reported. Each of the treatment arms is clearly distinct from the untreated control group. Carboplatin treatment and TDRL-551 displayed similar growth inhibition of tumors. This demonstrates single agent anti-cancer activity of TDRL-551 in vivo that is consistent with the cellular assays reported above. Surprisingly, mice receiving carboplatin and TDRL-551 demonstrated the slowest tumor growth, consistent with TDRL-551 sensitizing cells to platinum. These data provide strong evidence that TDRL-551 can be used to sensitize NSCLC tumors to Pt-based therapy.

The experiments presented describe the synthesis, structure activity relationships and in vitro and cellular activity of novel reversible RPA inhibitors in EOC and NSCLC. Both single agent activity and synergy in combination with DNA damaging chemotherapeutic agents; cisplatin and etoposide have been demonstrated. In vivo data demonstrate no overt toxicity and good clinical efficacy in combination with carboplatin in a NSCLC xenograft model. This represents the first in vivo deployment of a small molecule inhibitor targeting the RPA-DNA interaction.

The SARs defined the necessary substituents for activity while maintaining excellent bioavailability. These data demonstrate that to achieve in vivo activity a balance between potency and bioavailability can lean towards lower affinity as long as PK parameters allow clinically effective concentrations to be maintained. This balance is especially important in targeting RPA an essential protein with homozygous mutations being embryonically lethal in mice, while heterozygous mutants having an early predisposition to cancer. No loss of function mutation for RPA has been reported in humans, and genetic knockdown of RPA affects cellular viability. Consequently, targeting RPA could have potential negative effects on rapidly dividing healthy cells, such as gut epithelial, hematopoietic, or hair follicle, and it could lead to unwanted side effects.

For this reason, exploiting the separation of function phenomena in RPA in a manner amenable for therapeutic intervention is crucial. Mouse toxicity studies indicate no significant overall change in body weight for doses up to 200 mg/kg, but show anti-tumor activity at the same dosage in a lung cancer xenograft model. Since cancer cells are undergoing an abnormal unregulated rate of proliferation, it is likely they are in a state of replicative stress and their dependence on RPA can be used to obtain a therapeutic window without harming the normal cells. This can also be understood by analogy to an oncogene addiction model, in which cancer cells have a higher dependence on the oncogene compared to normal cells and hence can be selectively targeted. Finally, RPA's overexpression has been correlated with multiple cancers like breast, lung and colon, and it has also been associated with metastasis. Thus, clinical reports of altered RPA expression in a variety of cancers make RPA a promising novel therapeutic target.

It is also important to elucidate whether the inhibitors exclusively impair the repair function of RPA without compromising its role in replication. Previously published data with inhibitor TDRL-505 demonstrate a G1 cell cycle arrest, however the cells that are already in S-phase progress through the replication phase. This indicates that the inhibitors are either blocking the initial phase of replication initiation or early origin firing and inhibiting the transition from G1 to S phase, or causing an alteration in the DNA damage checkpoint signaling. In either case, the 505 class of inhibitors do not block progression through S-phase once the G1-S transition has occurred. It has also been demonstrated that 505 and 551 have a similar mechanism and target the DBD-A/B domain of RPA. Interestingly, a significant difference in the inhibition potency of TDRL-505 and TDRL-551 for RPA DBD-A/B was not observed. The improved potency of TDRL-551 for full length RPA could be due to its binding at other sites in RPA and thus the overall potency of the molecule could be a result of multiple binding sites.

The current results demonstrating synergy of TDRL-551 with Pt in an EOC cell line, along with published data showing synergy of TDRL-505 with Pt in a lung cancer cell line indicates that the RPA inhibitors of the present disclosure are impairing the repair function of RPA. The major limitation for successful treatment of a variety of cancers, including EOC, has been the tolerance and repair of Pt-DNA adducts and has been specifically correlated to increased repair in a variety of ovarian cancer cell lines. Hence, inhibiting DNA repair by targeting RPA could have a major significance for cancer therapy.

Also examined was the ability of TDRL-551 to synergize with etoposide, a topoisomerase II inhibitor. Etoposide treatment leads to both single and double stranded DNA breaks as well as stalling and collapse of replication forks. Inhibiting RPA's replication function could further enhance the number of DNA breaks produced on etoposide treatment and improve the effectiveness of the treatment. Although TDRL-505 has been previously shown to be highly synergistic with etoposide in lung cancer cells through a flow cytometry based Annexin-PI staining assay, its optimized analog, TDRL-551, showed modest synergy with etoposide at the highest fractions of cells affected (>0.8) in A2780 EOC cell line through colony formation assay.

Compound TDRL-551 may be more specific in targeting the repair function of RPA than its predecessor TDRL-505 and hence doesn't significantly impact replication and only mildly synergizes with etoposide. Alternatively, the differences may be a function of the cell lines used and cancer types being investigated. While cisplatin and etoposide are the standard drugs used in treatment against lung cancer, the therapy for ovarian cancer involves the combination of platinum and taxol. Etoposide is not a first line therapy for EOC and hence improving its effectiveness may be limited based on the cancer. Lastly, the differing synergy outcomes may be a consequence of the type of assay performed in each case. Despite these caveats, the important finding is that RPA inhibition with TDRL-551 synergizes with cisplatin in EOC and may provide an avenue to increase sensitivity to platinum in the clinic.

RPA inhibitors can be used as DNA repair inhibitors to overcome resistance to platinum based chemotherapies. Inhibiting DNA repair with SMIs can be used in combination with Pt both at first line and second line stage of therapy. In first line therapy, Pt in combination with RPA inhibitors could lead to maximum effectiveness by killing the majority of cancer cells, which are now sensitized to Pt due to inhibition of DNA repair. This may certainly still lead to some surviving cancer cells that are resistant to the treatment due to other mechanisms, such as reduced uptake of platinum, increased drug efflux, or increased expression of proteins like glutathione that bind and inactivate Pt in the cells. However, since there will be less number of surviving cancer cells to relapse with platinum resistant forms, any increase in the effectiveness of the first line therapy would lead to an improved progression free survival (PFS), which can be clinically significant.

As second line therapy, RPA inhibitors can be used in combination with Pt to re-sensitize the platinum resistant cancers, also leading to an increase in PFS. It is important to mention that platinum based chemotherapy is not the only scope for the utility of RPA inhibitors. Since RPA plays a variety of roles in different pathways, its other functions can also be targeted. For instance, RPA inhibitors can be used in combination with radiation therapy that induces double stranded breaks (DSB). Thus, inhibiting RPAs role in HR-dependent DSB repair would be expected to enhance the effectiveness of radiotherapy. RPA inhibitors can be used in a multitude of platforms with a special focus in the area of cancer therapy.

Certain materials and methods for inhibiting replication protein A and uses thereof are disclosed and claimed in U.S. Pat. No. 8,859,532 and U.S. patent application Ser. No. 14/470,585, the disclosures of which are both hereby expressly incorporated herein by reference in their entirety.

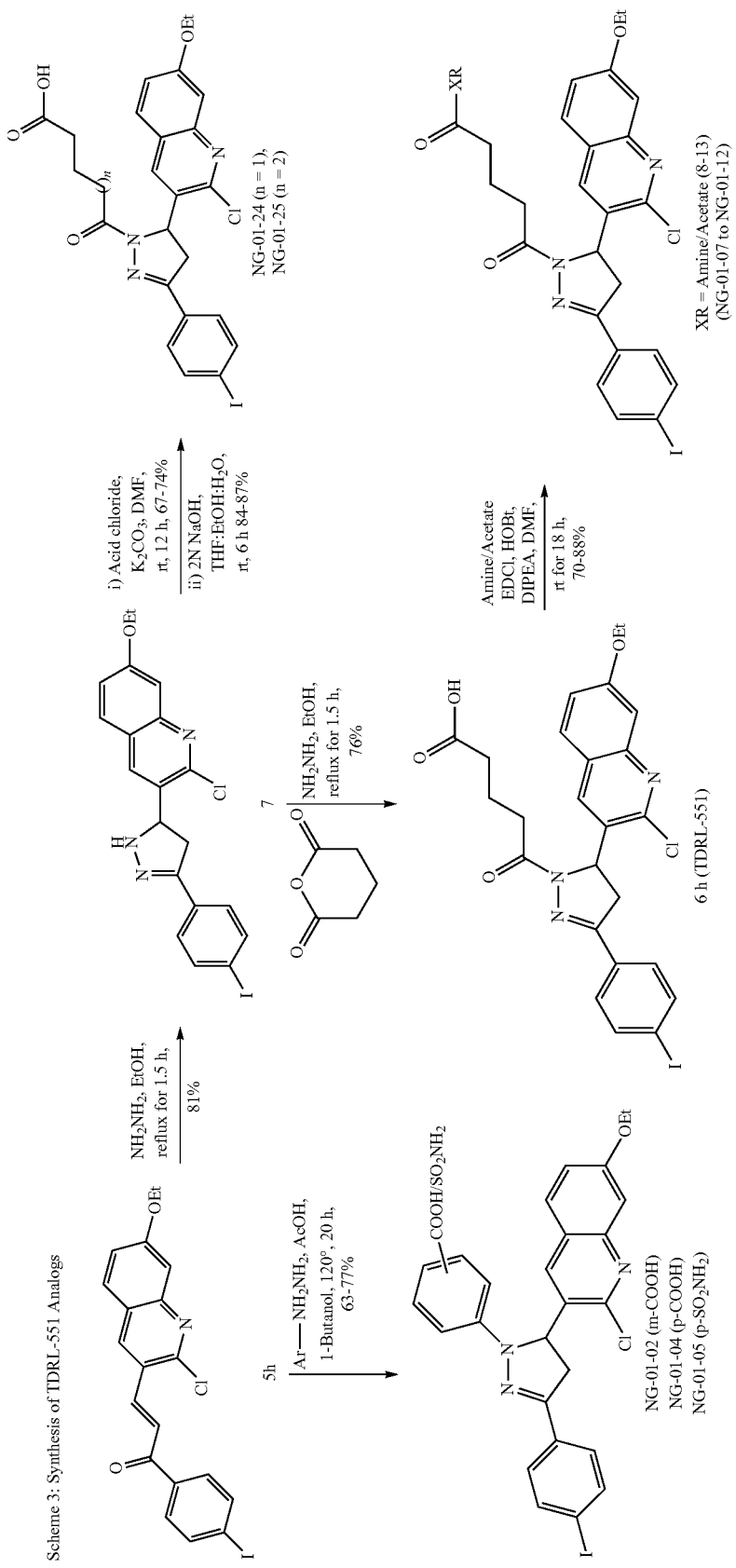
Scheme 3: Synthesis of TDRL-551 Analogs

TABLE 3

Molecular weights and RPA inhibitory activity of TDRL-505, TDRL-551 and its analogs.

| COMPOUNDS | Mol. Wt. | RPA INHIBITORY ACTIVITY |
|---|---|---|
| 505 | | + |
| 551 | | ++ |
| NG-01-02 | 597.83 | |
| NG-01-04 | 597.83 | |
| NG-01-05 | 632.9 | |
| NG-01-07 | 660.93 | |
| NG-01-08 | 673.97 | |
| NG-01-09 | 630.9 | |
| NG-01-10 | 644.93 | |
| NG-01-11 | 619.87 | − |
| NG-01-12 | 681.94 | − |
| NG-01-21 | 633.9 | − |
| NG-01-22 | 647.93 | − |
| NG-01-24 | 605.85 | +++ |
| NG-01-25 | 619.87 | ++ |
| NG-01-36 | 625.84 | − |
| NG-02-126F2 | 535.97 | +++ |
| NG-02-136 | 562.01 | ++ |
| MJ-01-06 | 575.82 | +/− |
| MJ-01-24 | 510.92 | +/− |
| MJ-01-26 | 481.93 | +/− |
| MJ-01-30/30R | 480.94 | +++ |
| MJ-01-40 | 509.94 | ++ |

The structural formulas of TDRL-551 analogs, NG-01-04, NG-01-02, NG-01-24 and NG-01-25 are shown, respectively, as follows:

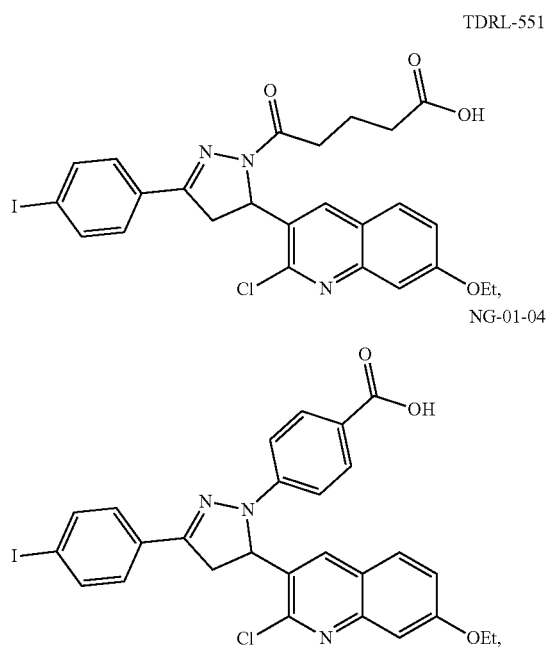

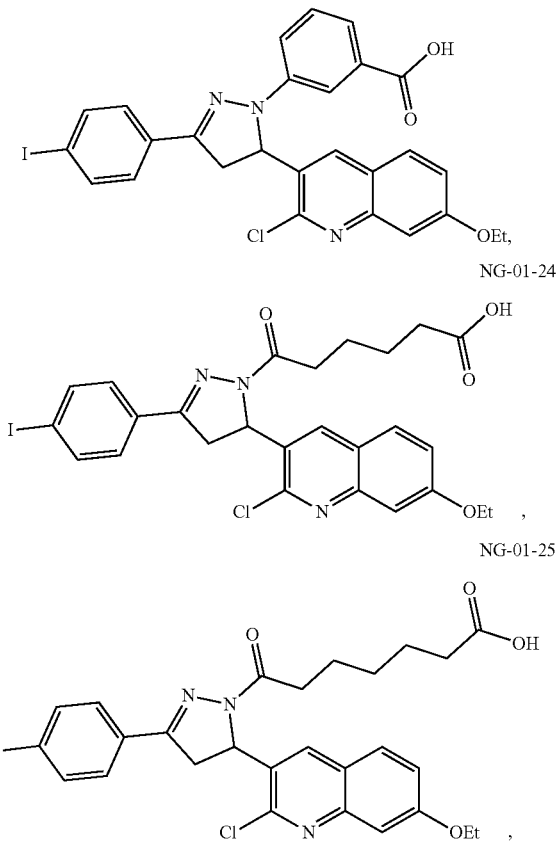

Figure 14:
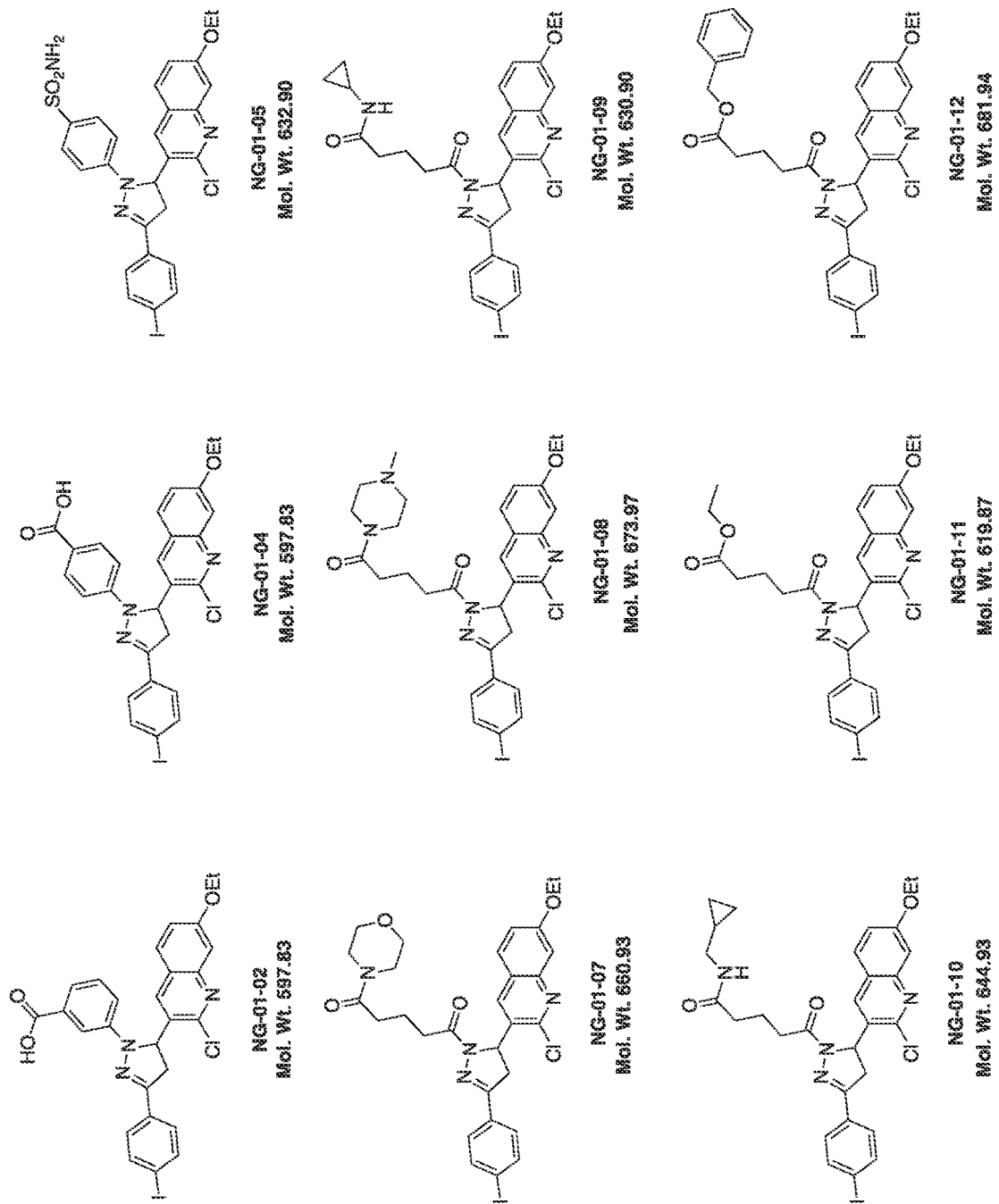
FIG. 14 provides structural formulas of TDRL-551 analogs.
Figure 15:
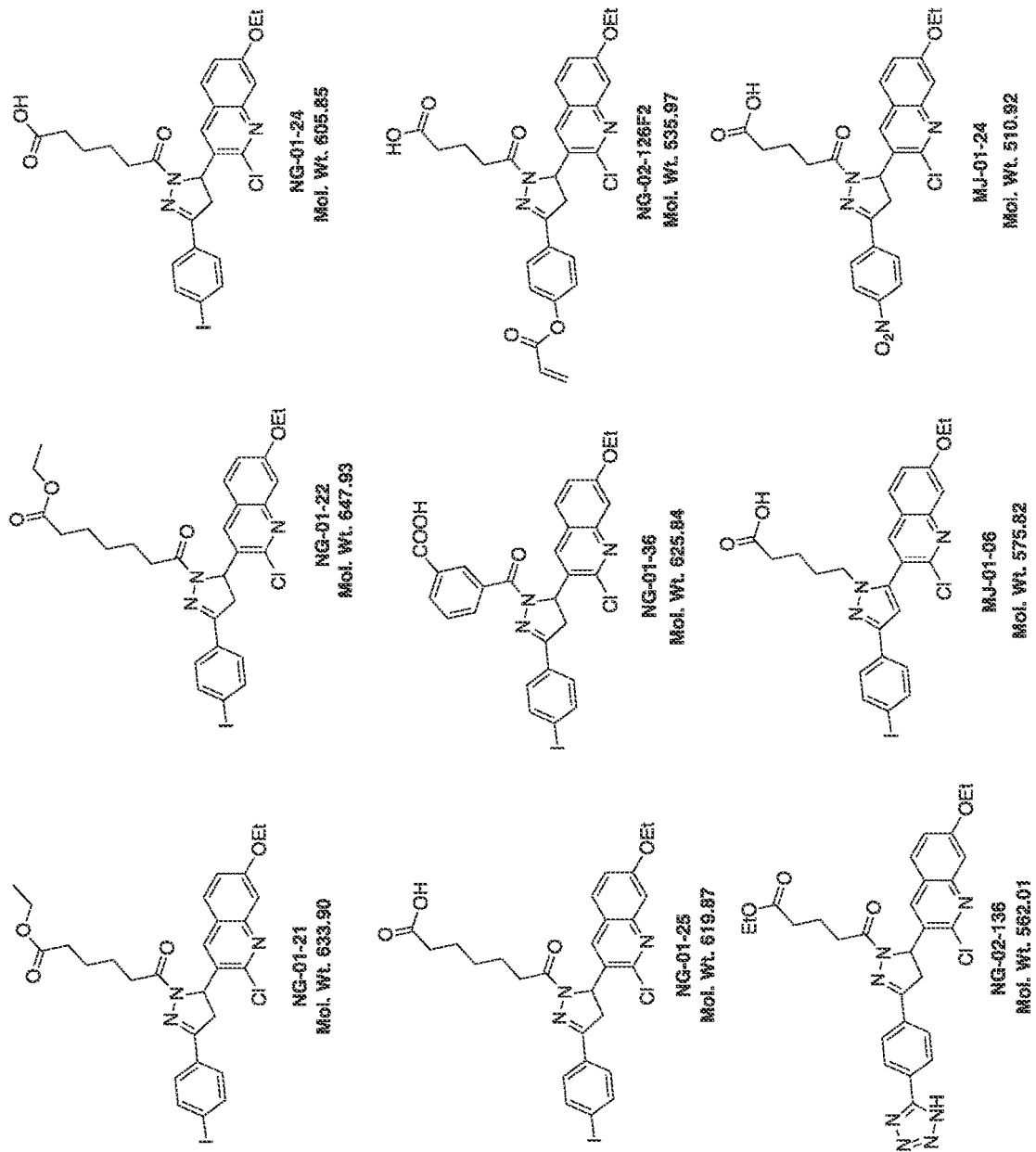
FIG. 15 provides structural formulas of TDRL-551 analogs.

Referring now to FIG. 14 to FIG. 16, additional structural formulas of TDRL-551 analogs are shown.

Figure 17:
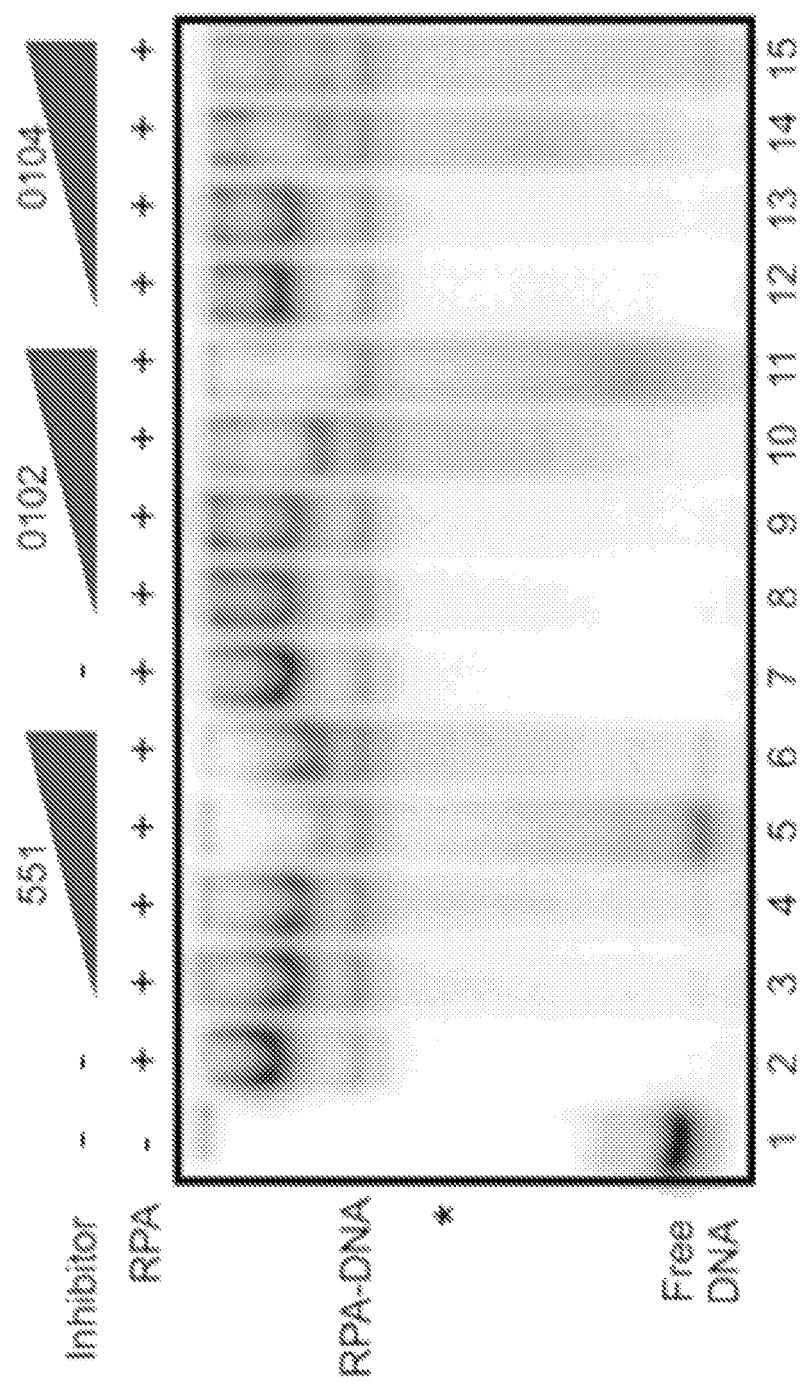
FIG. 17 shows a blot in which TDRL-551 and its analogs (NG-01-02 and NG-01-04) were screened using the Electrophoretic Mobility Shift Assays (EMSA) for RPA-DNA inhibition activity.
Figure 18:
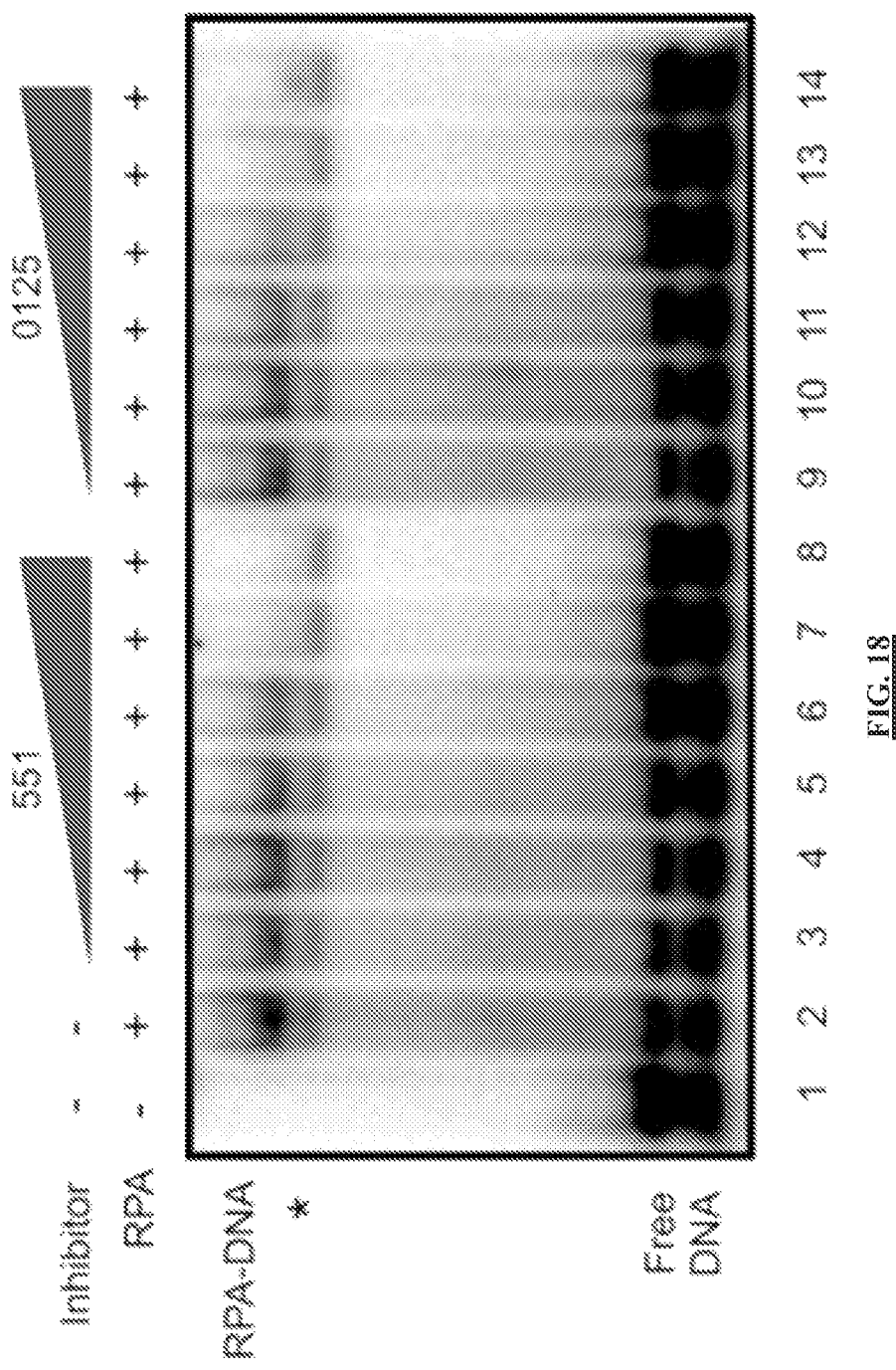
FIG. 18 shows a blot in which TDRL-551 and its analog (NG-01-25) were screened using the Electrophoretic Mobility Shift Assays (EMSA) for RPA-DNA inhibition activity.

Referring now to FIG. 17 and FIG. 18, TDRL-551 and its analogs were screened using the EMSA assay for RPA-DNA inhibition activity. The free DNA and RPA-DNA complexes are indicated. The asterisk indicated the position of the *E. coli* SSB-DNA complex.

Figure 19:
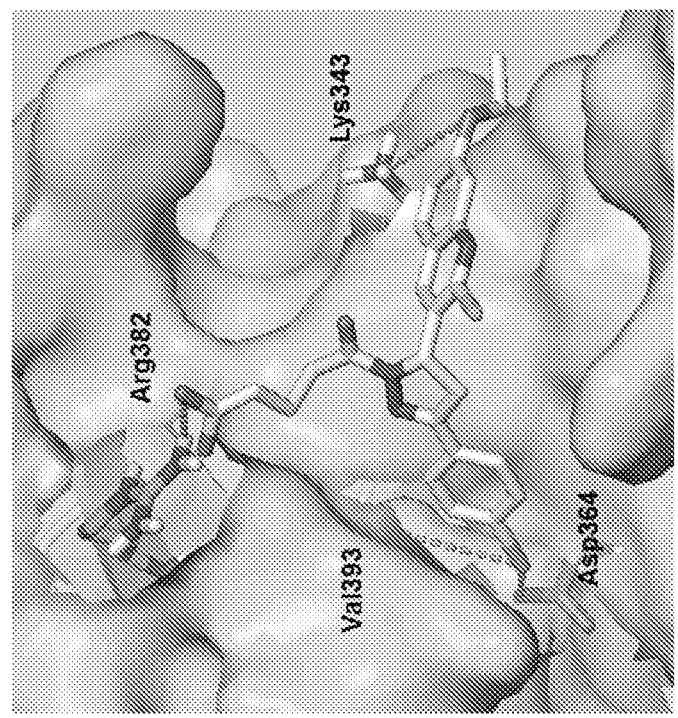
FIG. 19 provides a diagram showing molecular interactions/binding site of TDRL-551-RPA.
Figure 19:
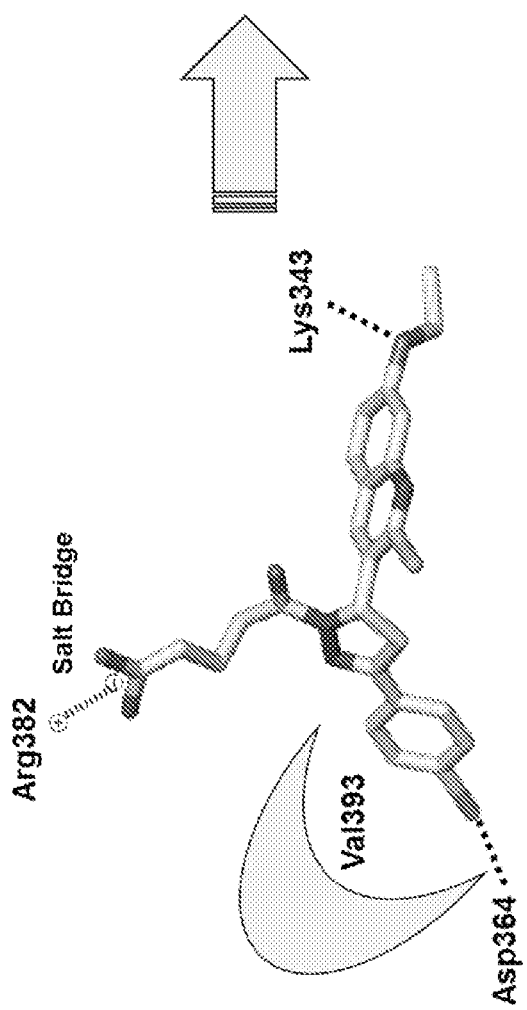

Referring now to FIG. 19, a schematic diagram shows molecular interactions between TDRL-551 and RPA, and a binding site of TDRL-551 in RPA.

Figure 20:
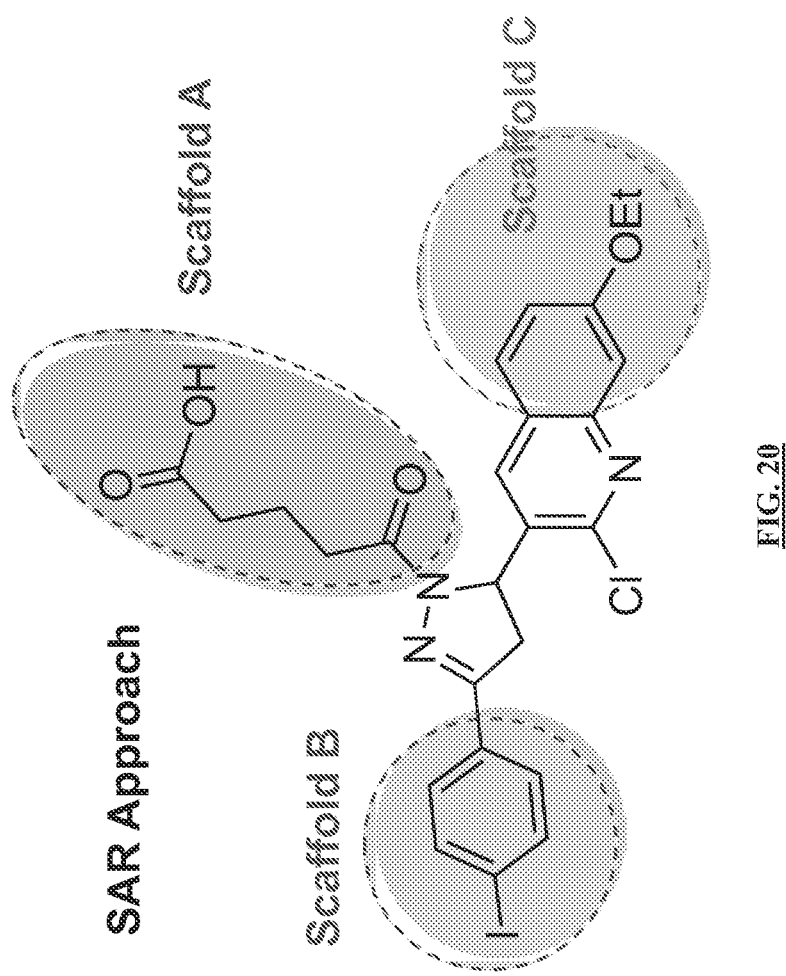
FIG. 20 provides a diagram showing structure activity relationships (SAR) approach.

Referring now to FIG. 20, a diagram shows a SAR approach using 3 sub-pockets to increase potency and selectivity.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

I claim:
1. A compound of the Formula

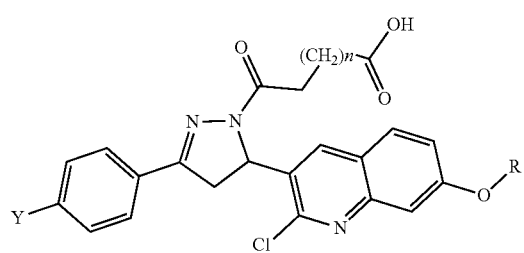

wherein, R is $C_1$-$C_6$ alkyl;
Y is iodo; and
n is 1, 2, or 3;
or a pharmaceutically acceptable salt thereof.

2. A compound selected from the group consisting of

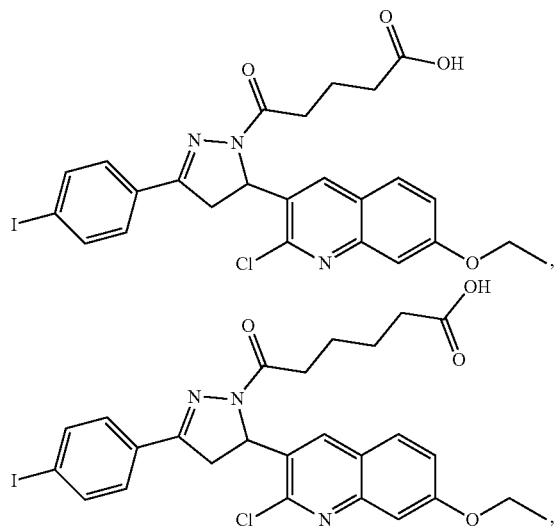

and

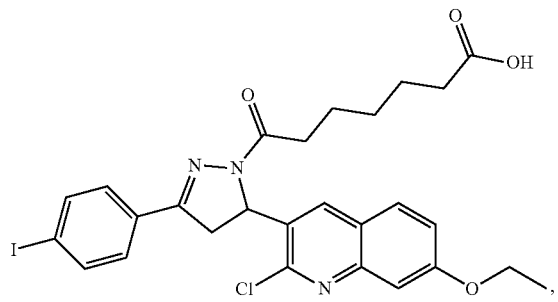

or a pharmaceutically acceptable salt thereof.

3. A compound of the formula

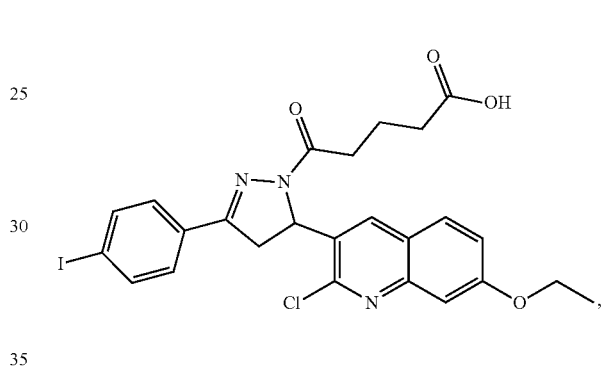

or a pharmaceutically acceptable salt thereof.

4. The compound according to claim 1, wherein the compound at least partially inhibits Replication Protein A.

* * * * *

UNITED STATES PATENT AND TRADEMARK OFFICE
CERTIFICATE OF CORRECTION

PATENT NO. : 10,774,063 B2
APPLICATION NO. : 15/524830
DATED : September 15, 2020
INVENTOR(S) : John J. Turchi It is certified that error appears in the above-identified patent and that said Letters Patent is hereby corrected as shown below:

In the Specification

The Statement of Governmental Rights should read:
This invention was made with government support under CA180710, CA162648, and CA247370 awarded by the National Institutes of Health. The government has certain rights in the invention.

Signed and Sealed this
Twenty-ninth Day of November, 2022

Katherine Kelly Vidal
*Director of the United States Patent and Trademark Office*